US008574843B2

(12) United States Patent
Fratamico et al.

(10) Patent No.: US 8,574,843 B2
(45) Date of Patent: Nov. 5, 2013

(54) GENETIC METHODS FOR SPECIATING CAMPYLOBACTER

(75) Inventors: Pina Fratamico, Elkins Park, PA (US);
Susumu Kawasaki, Tsukuba (JP);
Shinichi Kawamoto, Tsukuba (JP)

(73) Assignees: The United States of America, as represented by the Secretary of Agriculture, Washington, DC (US);
National Agriculture & Food Research Organization, Tsukuba Ibaraki (JP)

( * ) Notice: Subject to any disclaimer, the term of this patent is extended or adjusted under 35 U.S.C. 154(b) by 860 days.

(21) Appl. No.: 11/705,398

(22) Filed: Feb. 12, 2007

(65) Prior Publication Data

US 2010/0092946 A1    Apr. 15, 2010

(51) Int. Cl.
*C12Q 1/68*        (2006.01)
*C07H 21/04*       (2006.01)

(52) U.S. Cl.
USPC .............................. 435/6.12; 536/23; 536/24

(58) Field of Classification Search
USPC .................................. 435/6, 91.2; 536/24.33
See application file for complete search history.

(56) References Cited

PUBLICATIONS

Ragimbeau, C. et al. Development of a multiplex PCR gene fingerprinting method using gyrA and pflA polymorphisms to identify genotypic relatedness within *Campylobacter jejuni* species. J Appl Microbiol., vol. 85, pp. 829-838, 1998.*
Keller, J et al. Genetic diversity in fluoroquinolone and macrolide-resistant *Campylobacter coli* from pigs. Vetern. Microbiol., vol. 113, pp. 103-108, 2006.*
Menard, A et al. Development of a real-time fluorescence resonance energy transfer PCR to identify the main pathogenic *Campylobacter* spp. Clin. Microbiol. Infect., vol. 11, pp. 281-287, 2005.*
Taylor, DE et al. Cloning and nucleotide sequence of the gyrA gene from *Campylobacter fetus* subsp. fetus ATCC 27374 and characterization of Ciprofloxacin-resistant laboratory and clinical isolates. Antimicrobial Agents and Chemotherapy, vol. 41(3), pp. 665-671, 1997.*
Lowe et al. A computer program for selection of oligonucleotide primers for polymerase chain reactions. Nucleic Acids Research, vol. 18, No. 7, pp. 1757-1761, 1990.*
Atabay, H.I., et al., "The Prevalence of *Campylobacters* and *Arcobacter* in Broiler Chickens," *Journal of Applied Microbiology*, 1997, vol. 83, pp. 619-626.
Damborg, Peter, et al., "Occurrence of *Campylobacter jejuni* in Pets Living with Human Patients Infected with *C. jejuni*," *Journal of Clinical Microbiology*, Mar. 2004, pp. 1363-1364.
Engvall, E. O., et al., "Validation of a polymerase chain reaction/restriction enzyme analysis method for species identification of thermophilic *Campylobacters* isolated from Domestic and Wild Animals," *Journal of Applied Microbiology*, 2002, vol. 92, pp. 47-54.

Gorkiewicz, Gregor, et al., "Species-Specific Identification of *Campylobacters* by Partial 16S rRNA Gene Sequencing," *Journal of Clinical Microbiology*, Jun. 2003, pp. 2537-2546.
Hanninen, Marja-Liisa, et al., "Detection and Typing of *Campylobacter jejuni* and *Campylobacter coli*, and Analysis of Indicator Organisms in Three Waterborne Outbreaks in Finland," *Applied and Environmental Microbiology*, Mar. 2003, pp. 1391-1396.
Harrington, Clare S., et al., "Evidence for Recombination in the Flagellin locus of *Campylobacter jejuni*: Implications for the Flagellin Gene Typing Scheme," *Journal of Clinical Microbiology*, Sep. 1997, pp. 2386-2392.
Harrington, C.S,. et al., "Inter-laboratory evaluation of Three flagellin PCR/RFLP Methods for Typing *Campylobacter jejuni* and *C. coli*: the CAMPYNET experience," Journal of Applied Microbiology, 2003, vol. 95, pp. 1321-1333.
Keramas, Georgios, et al., "Developement of a sensitive DNA microarray suitable for Rapid Detection of *Campylobacter* spp," *Molecular and Cellular Probes*, 2003, vol. 17, pp. 187-196.
Koenraad, P.M. F., et al., "The Speciation and subtyping of *Campylobacter* isolates from sewage plants and waste water from a connected poultry abattoir using molecular techniques," *Epidemil. Infect*, 1995, vol. 115, pp. 485-494.
Logan J.M.J., et al., "Rapid Identification of *Campylobacter* spp. By Melting Peak Analysis of Biprobes in Real-Time PCR," *Journal of Clinical Microbiology*, Jun. 2001, pp. 2227-2232.
Mandrell, Robert E. et al.., "Speciation of *Campylobacter coli, C. jejuni, C. helveticus, C. lari, C. sputorum,* and *C. Upsaliensis* by Matrix-Assisted Laser Desorption Ionization-Time of Flight Mass Spectrometry," *Applied and Enviromental Microbiology*, Oct. 2005, vol. 71, No. 10, pp. 6292-6307.
Manning, Georgina, et al., "Multilocus Sequence Typing for Comparison of Veterinary and Human Isolates of *Campylobacter jejuni*," *Applied and Environmental Microbiology*, Nov. 2003, vol. 69, vol. 11, pp. 6370-6379.
Moser, I.., et al., "Genomic Heterogenteity and O-Antigenic Diversity of *Campylobacter upsaliensis* and *Campylobacter heveticus* Strains Isolated from Dogs and Cats in Germany," Journal of Clinical Microbiology, Jul. 2001, vol. 3 9, No. 7, pp. 2548-2557.

(Continued)

Primary Examiner — Christopher M Babic
Assistant Examiner — Aaron Priest
(74) Attorney, Agent, or Firm — John D. Fado; Evelyn M. Rabin

(57)  ABSTRACT

The phylogeny of twelve *Campylobacter* species was determined based on partial (1020-bp) gyrB gene sequences. Methods have been described for detection and speciation of *Campylobacter*, including 16S rRNA sequence analysis. However, gyrB provides a better resolution than the 16S rDNA gene for *Campylobacter* species with interspecies sequence similarities ranging from 58.3 to 89.2% compared to those reported for the 16S rRNA gene (ranging from 89 to 99%). A universal primer set, designed to amplify a 900-bp fragment of the gyrB gene in *Campylobacter* spp., was developed and used for PCR-RFLP of 19 strains representing twelve *Campylobacter* species and resulted in unique digest patterns for all twelve *Campylobacter* species PCR assays for amplification of regions of the gyrB gene specific for each *Campylobacter* species were also developed. Using these PCR and PCR-RFLP methods results in unambiguous identification of the majority of *Campylobacter* species.

8 Claims, 7 Drawing Sheets

(56) References Cited

PUBLICATIONS

On, Stephen L.W., et al., "Identification of Taxonomic and Epidemiological relationships among *Campylobacter* species by numerical analysis of AFLP profiles," *FEMS Microbiology Letters*, 2000, vol. 193, pp. 161-169.

On, S.L.W. "Taxonomy of *Campylobacter, Arcobaccter, Helicobacter* and related bacteria: current status, future prospects and immediate concerns," *Journal of Applied Microbiology*, 2001, vol. 90, pp. 1s-15s.

Stern, Norman., et al., "Flagellin a Gene Restriction Fragment Length Polymorphism Patterns of *Campylobacter* spp. Isolates from Broiler Production Sources," *Avian Diseases*, 1997, vol. 41, pp. 899-905.

Van Doom, Leen-Jan, et al., "Rapid Identification of Thermotolerant *Campylobacter jejuni, Campylobacter coli, Campylobacter lari,* and *Campylobacter upsaliensis* from Various Geographic Locations by a GTPase-Based PCR-Reverse Hybridization Assay," *Journal of Clinical Microbiology*, Jun. 1999, vol. 37, No. 6, pp. 1790-1796.

Volokhov, Dmitriy, et al., "Microarray-Based Identification of Thermophilic *Campylobacter jejuni, C. coli, C. lari,* and *C. upsaliensis*," *Journal of Clinical Microbiology*, Sep. 2003, vol. 41, No. 9, pp. 4071-4080.

Yamada, Shoichi, et al., "Cloning and Nucleotide Sequence Analysis of gyrB og *Bacillus cereus, B. thuringiensis, B. mycoides,* and *B. anthracis* and their Application to the Detection of *B. cereus* in Rice," *Applied and Environmental Microbiology.*, Apr. 1999, vol. 65, No. 4, pp. 1483-1490.

Yamamoto, Satoshi., et al., "PCR Amplification and Direct Sequencing of gyrB Genes with Universal Primers and Their Application to the Detection and Taxonomic Analysis of *Pseudomonas putida* Strains," *Applied and Enviornmental Microbiology*, Mar. 1995, vol. 61, No. 3, pp. 1104-1109.

\* cited by examiner

GENETIC METHODS FOR SPECIATING *CAMPYLOBACTER*

BACKGROUND OF THE INVENTION

1. Field of the Invention

This invention relates to the gyrase B gene which encodes for the subunit B protein of DNA gyrase, a type II topoisomerase that catalyzes the negative supercoiling of bacterial DNA, sequence polymorphisms in the *Campylobacter* gyrB gene, and species-specific PCR (polymerase chain reaction) assays and PCR-RFLP (PCR-restriction fragment length polymorphism) using the restriction enzymes DdeI and XspI for differentiation of *Campylobacter* species, and a method of speciating *Campylobacter*.

2. Description of the Relevant Art

*Campylobacter* spp. are the most common cause of bacterial gastrointestinal infection in the United States, Japan, and other developed nations. Infections have the highest incidence in infants, young children, and in adults 20 to 40 years of age. Travel to developing countries is a major risk factor for acquiring *Campylobacter* infections. The majority of human infections due to *Campylobacter* spp. are sporadic or occur in small family clusters rather than large outbreaks, rendering identification of sources of infection through epidemiological investigations difficult. There are numerous animal reservoirs for *Campylobacter* spp., including cattle, sheep, poultry, and swine; however, the major animal source for sporadic infections is poultry (Corry et al. 2001. *J. Appl. Microbiol.* 90:96S-114S; Manning et al. 2003. *Appl. Environ. Microbiol.* 69: 6370-6379; Nielsen, E. M. 2002. *Lett. Appl. Microbiol.* 35: 85-89). A recent population-based, case-control study conducted by Friedman et al. (2004. *Clin. Infect. Dis.* 38 (Suppl 3): 285-296) indicated that consuming poultry, particularly prepared in restaurants, is a major risk factor for sporadic human *Campylobacter* infection in the U.S. Household pets, including dogs and cats, are also a source of *Campylobacter* infections (Damborg et al. 2004. *J. Clin. Microbiol.* 42: 1363-1364; Moser et al. 2001. *J. Clin. Microbiol.* 39: 2548-2557). In addition to animal sources, contaminated vegetables and shellfish have also been linked with *Campylobacter* infection (Altekruse et al. 1994. *J. Am. Vet. Assoc.* 204: 57-61; Jacobs-Reitsma, W. 2000. In: *Campylobacter*, Nachamkin and Blaser, eds., ASM Press, Washington, D.C., pages 467-481), and contaminated water supplies have been implicated in point-source outbreaks (Goossens et al. 1995. *J. Infect. Dis.* 172: 1298-1305; Hanninen et al. 2003. *Appl. Environ. Microbiol.* 69: 1391-1396).

The genus *Campylobacter* consists of 16 species and six subspecies (On, S. L. W. 2001. *J. Appl. Microbiol.* 90: 1S-15S). Some species mainly cause disease in animals, including cattle, swine, sheep, dogs, and cats (Lastovica et al. 2000. In: *Campylobacter*, Nachamkin and Blaser, eds., ASM Press, Washington, D.C., pages 89-120). The thermophilic species, *C. jejuni, C. coli, C. lari*, and *C. upsaliensis*, but in particular *C. jejuni*, account for the majority of human infections; however, other species have been linked with diarrheal illness, periodontal disease (*C. concisus, C. gracilis, C. rectus*, and *C. showae*), meningitis, and septicemia in humans (Lastovica et al., supra). As examples, *C. lari* was associated with a water-borne outbreak of gastroenteritis (Borczyk et al. 1987. *Lancet* 1: 164-165), *C. upsaliensis* caused an outbreak in four day care centers in Brussels, affecting 44 children (Goossens et al., supra), *C. jejuni* and *C. fetus* subsp. *fetus* caused an outbreak associated with raw milk in individuals who attended a banquet in Wisconsin (Klein et al. 1986. *JAMA* 255: 361-364), and a number of different species have been isolated from stools of diarrheic patients (Lastovica et al., supra). Because of technical limitations in current cultural and phenotypic methods employed for detection, isolation, and typing of *Campylobacter*, non-*jejuni* species are likely under-reported in clinical specimens. Further research is needed to identify sources of infection, routes of transmission, and disease syndromes associated with non-*jejuni Campylobacter* species.

A number of methods have been described for detection and speciation of *Campylobacter*, including 16S rRNA sequence analysis (Gorkiewicz et al. 2003. *J. Clin. Microbiol.* 41: 2537-2546) and PCR-based assays for detection of single species or for species differentiation based on rRNA genes (Junior et al. 2003. *Pesqui. Odontol. Bras.* 17: 142-146, 21). Real-time PCR assays using fluorescence resonance energy transfer (FRET) probes targeting 16S rRNA sequences in *Campylobacter* spp. followed by melting peak analysis were used for detection and identification of different species (Logan et al. 2001. *J. Clin. Microbiol.* 39: 2227-2232). A reverse hybridization line probe assay based on use of species-specific probes targeting a putative GTPase could distinguish *C. jejuni, C. coli, C. lari*, and *C. upsaliensis* (van Doorn et al. 1999. *J. Clin. Microbiol.* 37: 1790-1796). On and Harrington (2000. *FEMS Microbiol. Lett.* 193: 161-169) distinguished *Campylobacter* species using an amplified fragment length polymorphism (AFLP)-based technique. However, the complex nature of the AFLP patterns that were generated rendered interpretation of results difficult, and the high cost of the equipment required may preclude the use of this technique in many research laboratories. Recently, Mandrell et al. (2005. *Appl. Environ. Microbiol.* 71: 6292-6307) described a method for speciating *C. coli, C. jejuni, C. helveticus, C. lari, C. sputorum*, and *C. upsaliensis* using matrix-assisted laser desorption ionization-time of flight mass spectrometry. A PCR-microarray method based on PCR amplification of *Campylobacter* species-specific genes and rRNA regions followed by hybridization to immobilized probes has been developed (Kerama et al. 2003. *Mol. Cell Probes* 17: 187-196; Volokhov et al. 2003. *J. Clin. Microbiol.* 41: 4071-4080).

Restriction enzyme analysis of PCR amplicons, known as PCR-restriction fragment length polymorphism (PCR-RFLP), is a useful tool for molecular characterization of food-borne pathogens, including differentiation of thermophilic *campylobacters* (Engvall et al. 2002. *J. Appl. Microbiol.* 92: 47-54) After amplification, the PCR product is digested using one or more restriction enzymes to produce fragments of specific sizes based on the DNA sequence of the gene. The PCR-RFLP technique based on the flagellar flaA and/or flaB genes has been used for speciation and subtyping of *Campylobacter* strains (Harrington et al. 2003. *J. Appl. Microbiol.* 95: 1321-1333; Koenraad et al. 1995. *Epidemiol. Infect.* 115: 485-494; Stern et al. 1997. *Avian Dis.* 41: 899-905). Intra- and inter-genomic recombination of the flaA and flaB genes, however, may contribute to the variability seen when this method is used (Harrington et al. 1997. *J. Clin. Microbiol.* 35: 2386-2392). The development of genotypic methods with the ability to precisely discriminate among the different species of *Campylobacter* is essential for effective monitoring and surveillance to determine the prevalence of these organisms in the environment and for defining the epidemiology of human infections.

The gyrase B gene encodes for the subunit B protein of DNA gyrase, a type II topoisomerase that catalyzes the negative supercoiling of bacterial DNA. Yamamoto and Harayama (1995. *Appl. Environ. Microbiol.* 61: 1104-1109) found that the frequency of base substitutions in gyrB was higher than that of 16S rRNA within the species *Pseudomonas putida*, thus gyrB has a higher ability than 16S rRNA to distinguish bacterial species within a genus. Species identification and detection methods based on gyrB have been developed for *Bacillus* spp. and *Vibrio* spp. (Venkateswaren et al. 1998. *Appl. Environ. Microbiol.* 64: 681-687; Yamada et al. 1999. *Appl. Environ. Microbiol.* 65: 1483-1490). There exists a need for specific primers and methods capable of specifically identifying and differentiating pathogenic *Campylobacter* species.

SUMMARY OF THE INVENTION

We have discovered oligonucleotide sequences which are capable of identifying sequence polymorphisms in the *Campylobacter* gyrB gene and differentiating closely related pathogenic *Campylobacter* species when used in simple and rapid species-specific PCR assays and PCR-RFLP.

In accordance with this discovery, it is an object of the invention to provide species-specific primers for PCR and PCR-RFLP for the specific detection and identification of closely related pathogenic *Campylobacter* species.

It is a further object of the invention to provide species-specific PCR assay methods and PCR-RFLP methods for utilizing the novel primers.

It is a still further object of the invention to provide a kit for use in the detection and differentiation of closely related *Campylobacter* species.

Other objects and advantages of this invention will become readily apparent from the ensuing description.

DETAILED DESCRIPTION OF THE INVENTION

Figure 1:
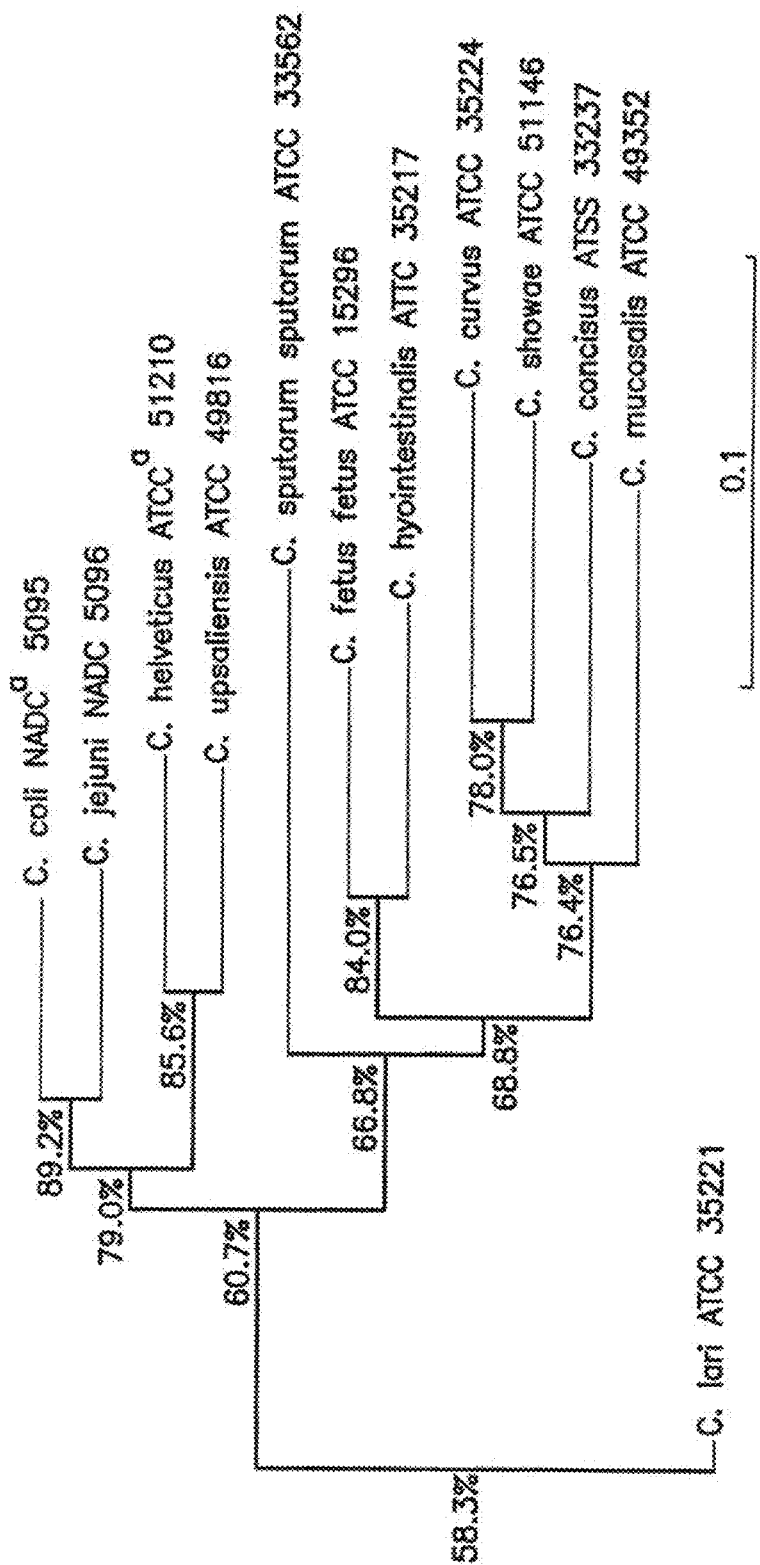
FIG. 1 shows a dendrogram of *Campylobacter* strains calculated from data for 1020 bp of the gyrB gene using the neighbor-joining method. Bar, 0.1 changes per nucleotide position.

The unambiguous identification of *Campylobacter* species is difficult because these pathogens are slow growing, fastidious organisms, which display few differential phenotypic properties (On, S. L. W. 1996. *Clin. Microbiol. Rev.* 9: 405-422.). Conventional classification methods for *Campylobacter*, *Arcobacter*, and *Helicobacter* species include phenotypic tests, for example, based on antibiotic resistance analysis, growth requirements, and biochemical tests. These tests often give ambiguous results and cannot be applied for identification of new or atypical species of *campylobacters*.

Alternatively, molecular techniques can be applied for typing and detection of microorganisms. Gorkiewicz et al. (supra) reported on the utility of 16S rDNA sequencing for identification of *Campylobacter* species. DNA sequencing for species identification is not practical because the cost is too high, and data analysis is somewhat complex. Therefore, we focused on the application of direct PCR and PCR-RFLP for the unambiguous identification of *Campylobacter* species based on the gyrB gene sequence analysis. The PCR is rapid, easy to perform, and is relatively inexpensive for practical use. Yamamoto and Harayama (supra) proposed use of the gyrB gene as a molecular taxonomic marker for bacterial species. The gyrB gene is a housekeeping gene and essential for DNA replication. This gene is present as a single copy on the bacterial genome, while the 16S rRNA genes are usually present as multiple copies in bacteria.

The major topology of the phylogenetic neighbor-joining tree constructed from the partial gyrB gene sequences used in this study was similar to the previously reported one constructed from the 16S rRNA gene sequences (Gorkiewicz et al., supra). However, gyrB provides higher resolution for *Campylobacter* species, with lower interspecies sequence similarities (ranging from 58.3 to 89.2%) compared to those reported for the 16S rRNA gene (ranging from 89 to 99%) (Gorkiewicz et al., supra). *C. fetus* subsp. *fetus* and *C. fetus* subsp. *venerealis* strains shared identical gyrB gene sequences, however, suggesting that gyrB may not be a suitable marker for *Campylobacter* identification at the subspecies level, Gorkiewicz et al. (supra) reported that the limitation of 16S rDNA analysis is the inability to differentiate *C. jejuni* and *C. coli* strains and atypical *C. lari* strains; both species shared identical 16S rRNA gene sequences, and nearly all strains of these taxa were assigned to a common cluster. The investigators commented that since *C. jejuni*, *C. coli*, and atypical *C. lari* are important pathogens, it is important to be able to differentiate these species. Since 16S rDNA analysis is not suitable to differentiate these species, other methods such as the PCR or methods based on phenotypic characteristics must be employed. On the contrary, our gyrB gene sequence analysis discriminated these three species. The strains of *C. jejuni* examined in the current study shared identical sequences and were clearly distinct from *C. coli*, though the two species had the highest similarity (89.2%) among the 12 *Campylobacter* species studied. Moreover, *C. lari* was positioned distinct from other species in the phylogenetic tree. These results further support the superiority of the gyrB gene over the 16S ribosomal DNA gene for *Campylobacter* species identification. It is noteworthy that the *C. fetus* and *C. hyointestinalis* strains tested had a 3-bp insertion different from other species in the same position of the gyrB gene (823-825), which resulted in an amino acid addition in the protein sequence.

Figure 2:
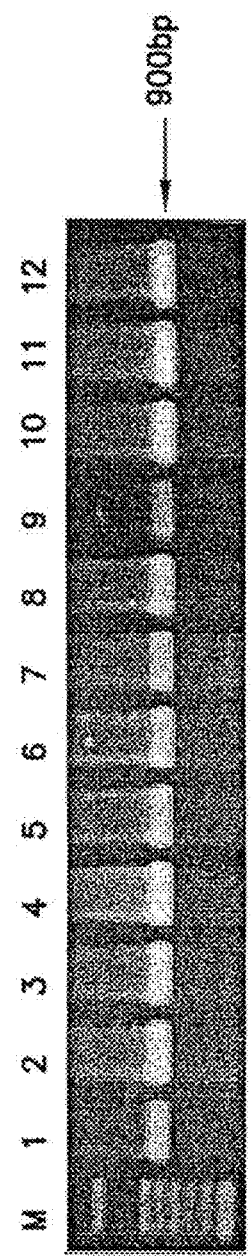
FIG. 2 shows the amplification fragments of the *Campylobacter* gyrB gene using a universal PCR mixture consisting of primers shown in Table 3. *C. jejuni* (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane 9), *C. helveticus* (lane 10), *C. upsaliensis* (lane 11), and *C. lari* (lane 12). Lane M, 100-bp molecular size markers.
Figure 4:
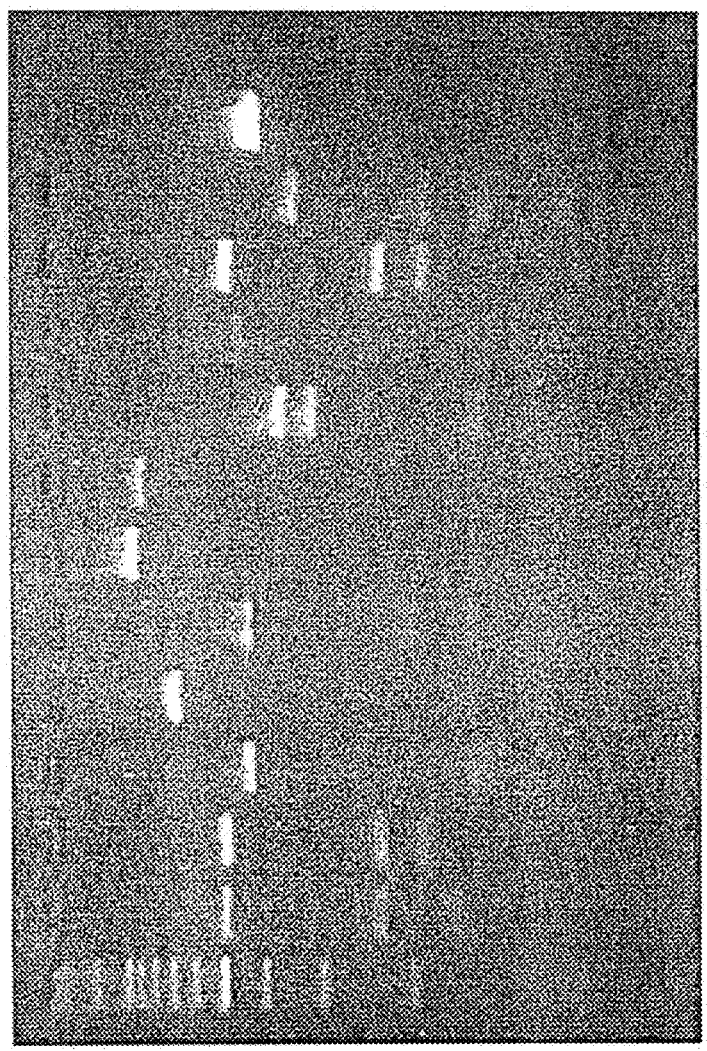
FIG. 4 depicts the PCR-RFLP (XspI) patterns of *C. jejuni* (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane 9), *C. helveticus* (lane 10), *C. upsaliensis* (lane 11), and *C. lari* (lane 12). Lane M, 100-bp molecular size markers.
Figure 5:
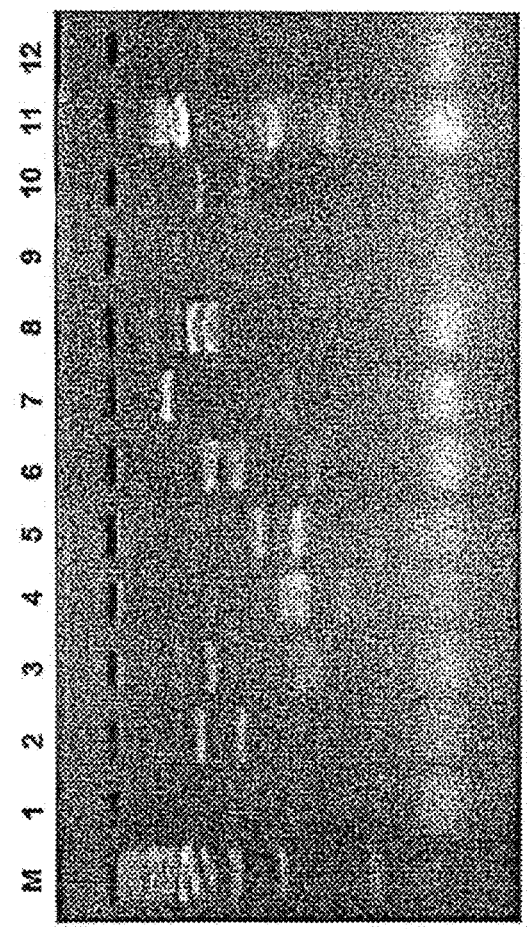
FIG. 5 depicts the PCR-RFLP (MboI and HindIII) patterns of *C. jejuni* (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane), *C. helveticus* (lane 10), *C. upsaliensis* (lane 11), and *C. lari* (lane 12). Lane M, 100-bp molecular size markers.

We designed the gyrB universal primer sets for PCR-RFLP typing of 12 *Campylobacter* species to ensure a high Tm (above 58° C. for 30 bases) and to amplify a 900-bp region in the gyrB gene in all of the species. The PCR conditions were optimized to achieve an ample amount of target amplicon for RFLP analysis (FIG. 2). PCR-RFLP analysis with DdeI or XspI displayed species-specific discrimination (FIGS. 3 and 4); however, DdeI could not discriminate between *C. concisus* and *C. sputorum*, since strains of both species generated fragments of 368 and 532 bp. Thus, if DdeI is chosen as the restriction enzyme for PCR-RFLP analysis of a presumptive *Campylobacter* isolate and fragments of 368 and 532 are generated, XspI could then be used to determine if the isolate is *C. concisus* or *C. sputorum*. Alternatively, a double digestion using MboI and HindIII can also be used to distinguish all of the *Campylobacter* species (FIG. 5).

Figure 6:
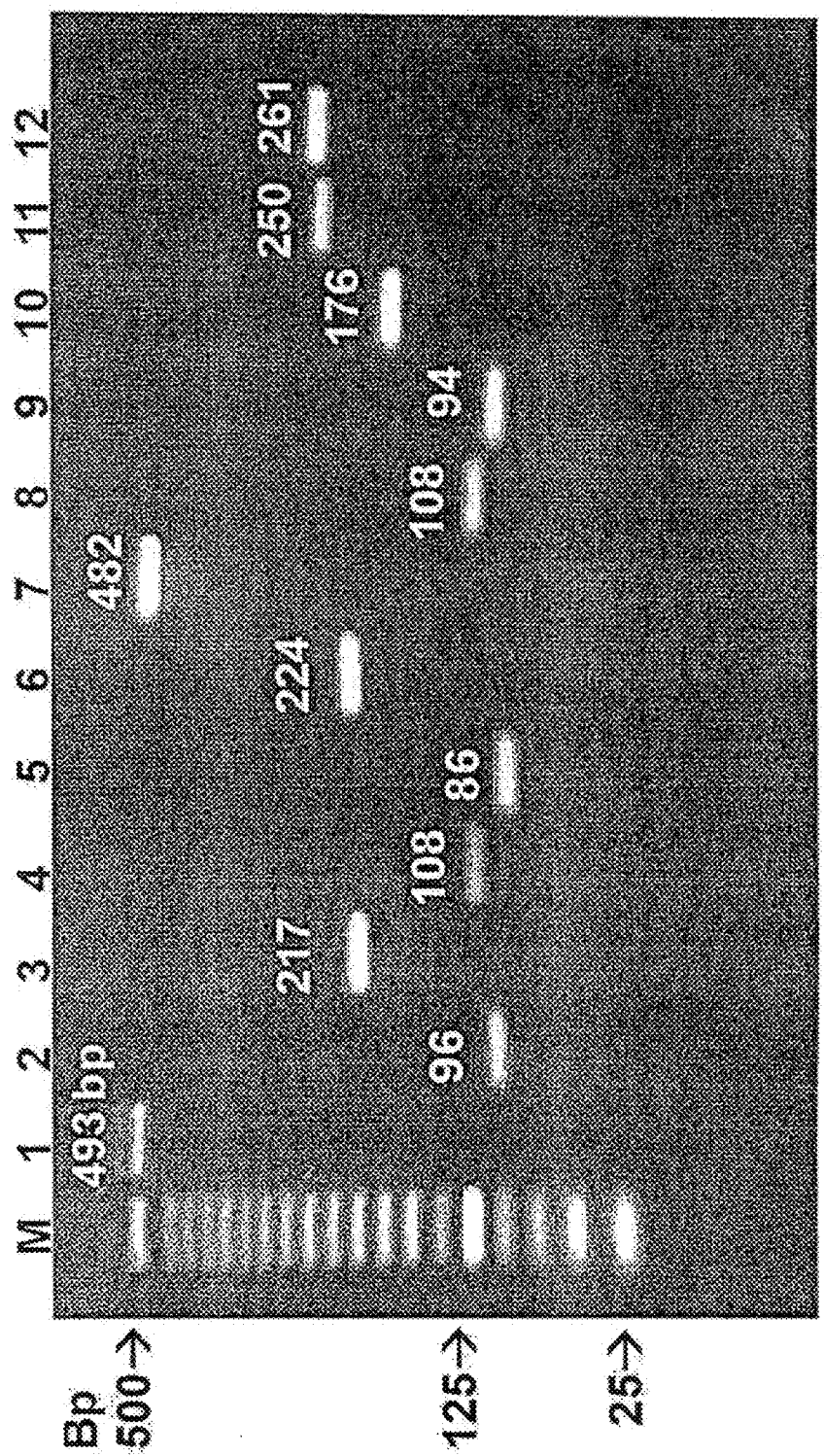
FIG. 6 depicts products obtained following *Campylobacter* species-specific PCR assays. *C. jejuni* (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane 9), *C. helveticus* (lane 10), *C. upsaliensis* (lane 11), and *C. lari* (lane 12). Lane M, 100-bp molecular size markers.

The gyro sequencing data made it possible to design species-specific primer sets for rapid detection and identification of *Campylobacter* species by direct PCR. The resulting species specific primers gave only the predicted sizes of the corresponding gyrB gene amplicons from target species (FIG. 6). The primer sequences were selected from gyrB regions of each species with mismatches of at least 7 bases with the gyrB gene sequence in the other species. Finally, highly species-specific identification by PCR was achieved due to the use of high annealing temperatures (65 to 69° C.) and the optimization of the $MgCl_2$ concentration.

Karenlapi et al. (2004. *J. Clin. Microbiol.* 42: 5731-5138) demonstrated that partial groEL sequencing and PCR-RFLP analysis had higher capability for *Campylobacter* species-specific identification than analysis based on 16S rRNA. In the current study, we demonstrated that partial gyrB gene sequencing, PCR-RFLP analysis, and direct PCR analysis with species-specific primer sets were applicable to unambiguously distinguish 12 *Campylobacter* species. The PCR-RFLP analysis relies on the presence of restriction recognition sites in the PCR amplified sequence. Therefore, the possibility that the results will be affected by errors that may occur during PCR amplification and the occurrence of spontaneous mutations in the target gene always exists. *Campylobacter* species identification can be confirmed by using the direct PCR method when a different PCR-RFLP profile pattern might appear in the future.

In conclusion, we sequenced a region of the gyrB gene in 12 *Campylobacter* species and developed PCR-RFLP and direct PCR assays, which should be more suitable for *Campylobacter* species identification than similar analyses based on the 16S rRNA gene. gyrB gene sequence information will be helpful in taxonomic studies of novel *Campylobacter* species. As new species of *Campylobacter* are discovered, the gyrB gene can be sequenced, and PCR primer sets specific for the new species can be designed. We are currently sequencing the gyrB gene of *C. gracilis, C. rectus, C. hominis,* and *C. lanienae*, and PCR and PCR-RFLP assays to detect and discriminate these species will be developed, as well. We believe that these methods will provide a very useful system for the rapid detection and unambiguous identification of *Campylobacter* species, which can replace the time-consuming conventional methods requiring use of laborious phenotypic and biochemical analyses. Further studies are needed to confirm the utility of the PCR-RFLP and direct PCR assays developed in this study for identification of *Campylobacter* species isolated from food, animal, and environmental samples.

As used herein, the terms "nucleic acid molecule", "nucleic acid sequence", "polynucleotide", and "polynucleotide sequence" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "Restriction Fragment Length of Polymorphism" (RFLP) is a technique in which organisms may be differentiated by analysis of patterns derived from cleavage of their DNA. If two organisms differ in the distance between sites of cleavage of a particular restriction endonuclease, the length of the fragments produced will differ when the DNA is digested with a restriction enzyme. The similarity of the patterns generated can be used to differentiate species and strains from one another. PCR can be used to amplify very small amounts of DNA to the levels required for RFLP analysis and is herein referred to as PCR-RFLP.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, NY or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "express" or "expression" is defined to mean transcription alone. The regulatory elements are operably linked to the coding sequence of the gene such that the regulatory element is capable of controlling expression of the gene.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product.

"protein" or "polypeptide" is a chain of amino acids arranged in a specific order determined by the coding sequence in a polynucleotide encoding the polypeptide. Each protein or polypeptide has a unique function.

The term "substantially pure" as used herein refers to a polypeptide that is substantially free of other proteins, lipids, carbohydrates or other materials with which it is naturally associated. One skilled in the art can purify the protein using standard techniques for protein purification. The purity of the polypeptide can also be determined by amino-terminal amino acid sequence analysis.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the thermal melting point (Tm) of the formed hybrid, and the G:C ratio within the nucleic acids. Stringency conditions can be adjusted to screen for moderately similar fragments, such as homologous sequences from distantly related organisms, to highly similar fragments, such as genes that duplicate functional enzymes from closely related organisms. Thus, isolated sequences that encode a gyrB polypeptide and which hybridize under stringent conditions to the gyrB sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal W method of alignment (Higgins and Sharp (1989. *CABIOS* 5:151-153) with the default parameters (GAP PENALTY=10, GAP LENGTH PENALTY=1.0), while default parameters for pairwise alignments using the Clustal W method were GAP PENALTY=10, GAP LENGTH PENALTY=1.0, Slow-Accurate unless otherwise indicated.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. The Tm is the temperature at which a population of double-stranded nucleic acid molecules becomes half dissociated into single strands (the mid-point). The equation for calculating the Tm of nucleic acids is well known in the art (See *Nucleic Acid Hybridization*, 1985, supra). As used herein, the term "stringency" is used in reference to the conditions of temperature, ionic strength, and the presence of other compounds such as organic solvents, under which nucleic acid hybridizations are conducted. As stated above, "stringency" typically occurs in a range from about 5° C. below the Tm of the specific sequence to about 20° C. to 25° C. below TM, depending upon the desired degree of stringency as otherwise qualified herein. As will be understood by those of skill in the art, a stringent hybridization can be used to identify or detect identical polynucleotide sequences or to identify or detect similar or related polynucleotide sequences.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in the amplification, but may alternatively be double stranded. If double stranded, the primer is first treated to separate its strands before being used to prepare extension products. The exact lengths of the primers will depend on many factors, including temperature, source of primer and the use of the method. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular protein. The skilled artisan, having the benefit of the sequences as reported herein, may now use all or a substantial portion of the disclosed sequences for purposes known to those skilled in this art.

By "variants" substantially similar sequences are intended. For nucleotide sequences, conservative variants include those sequences that, because of the degeneracy of the genetic code, encode the amino acid sequence of the gyrB polypeptide of the invention. Naturally occurring allelic variants such as these can be identified with the use of well-known molecular biology techniques, as, for example, with PCR.

EXAMPLES

Having now generally described this invention, the same will be better understood by reference to certain specific examples, which are included herein only to further illustrate the invention and are not intended to limit the scope of the invention as defined by the claims.

Example 1

Bacterial Strains

The sequences of the gyrB gene from a total of 19 strains of various species of *Campylobacter* were analyzed: 4 strains of *C. jejuni* (Table 1) and also *C. jejuni* RM1221 Acc. No. NC_003912 and *C. jejuni* subsp. *jejuni* NCTC 11168, Acc. No. NC_002163; *C. coli* NADC 5085 (National Animal Disease Center, Ames, Iowa); *C. concisus* ATCC 33237 (American Type Culture Collection, Manassas, Va.); *C. curvus* ATCC 35224; *C. showae* ATCC 51146; *C. mucosalis* ATCC 49352; *C. fetus* subsp. *fetus* ATCC 15296 and *C. fetus* NADC 5513; *C. fetus* subsp. *venerealis* NADC 5519; *C. hyointestinalis* ATCC 35217; *C. sputorum* biovar *sputorum* ATCC 33562; *C. helveticus* ATCC 51210; *C. upsaliensis* ATCC 49816; and *C. lari* ATCC 35221. These strains and other bacterial strains used in this study for determining the specificity of the PCR assays are listed in Table 1.

TABLE 1

Bacterial strains.

| Bacterial strain | Strain designation/source |
|---|---|
| C. jejuni subsp. jejuni | ATCC[a] 33250 |
| C. jejuni | NADC[b] 2682 |
| C. jejuni | NADC 5523 |
| C. jejuni | NADC 2812 |
| C. jejuni | NADC 5096 |
| C. coli | NADC 2681 |
| C. coli | NADC 5095 |
| C. coli | ATCC 33559 |
| C. lari | NADC 1945 |
| C. lari | NADC 3517 |
| C. lari | ATCC 35221 |
| C. concisus | ATCC 33237 |
| C. curvus | NADC 3221 |
| C. curvus | ATCC 35224 |
| C. mucosalis | NADC 3213 |
| C. mucosalis | NADC 3214 |
| C. mucosalis | NADC 3262 |
| C. mucosalis | ATCC 49352 |
| C. fetus | NADC 5513 |
| C. fetus fetus | ATCC 15296 |
| C. fetus fetus | NADC 436 |
| C. fetus fetus | NADC 1251 |
| C. fetus fetus | NADC 1254B |
| C. fetus venerealis | ATCC 19438 |
| C. fetus venerealis | NADC 5519 |
| C. hyointestinalis | NADC 2262 |
| C. hyointestinalis | ATCC 35217 |
| C. showae | ATCC 51146 |
| C. sputorum | NADC 4033 |
| C. sputorum fecalis | NADC 5533 |
| C. sputorum biovar sputorum | ATCC 33562 |
| C. rectus | NADC 3237 |
| C. rectus | ATCC 33238 |
| C. hominis | ATCC BAA-381 |
| C. helveticus | NADC 5532 |
| C. helveticus | ATCC 51210 |
| C. upsaliensis | NADC 5525 |
| C. upsaliensis | ATCC 49816 |
| C. upsaliensis | ATCC 49815 |
| C. gracilis | ATCC 33236 |
| H. pullorum | NADC 5535 |
| H. cholecystus | NADC 6910 |
| H. felis | NADC 6891 |
| H. cinaedi | NADC 3207 |
| H. cinaedi | ATCC BAA-76 |
| H. fennelliae | NADC 3211 |
| H. fennelliae | ATCC 35683 |
| H. bizzozeroni | NADC 6893 |
| H. bizzozeroni | NADC 6894 |
| H. muridarum | NADC 6895 |
| H. muridarum | NADC 6892 |
| H. pametensis | NADC 6900 |
| H. nemestrina | NADC 6904 |
| H. mustelae | NADC 3229 |
| H. canis | NADC 6899 |
| H. bilis | NADC 6897 |
| H. bilis | NADC 6896 |
| H. pylori | NADC 3222 |
| H. rappini | NADC 6915 |
| H. mustelae | NADC 3229 |
| A. cryaerophilus | NADC 3252 |
| A. cryaerophilus | NADC 2710 |
| A. butzleri | NADC 3545 |
| A. butzleri | NADC 3255 |
| A. butzleri | ATCC 49616 |
| A. skirrowii | NADC 3706 |
| A. skirrowii | NADC 3699 |
| A. skirrowii | NADC 3704 |
| E. coli O157:H7 | 380-94 FSIS[c] |
| E. coli O157:H7 | C984 CDC[d] |
| E. coli O157:H7 | B1409-C1 CDC |

TABLE 1-continued

Bacterial strains.

| Bacterial strain | Strain designation/source |
|---|---|
| S. Typhimurium | H3278 CDC |
| S. Typhimurium | G7601 CDC |
| S. Enteritidis | H3527 CDC |
| S. Enteritidis | H3526 CDC |
| Bacteroides ureolyticus | NADC 3167 |

[a]ATCC—American Type Culture Collection, Manassas, VA.
[b]NADC—National Animal Disease Center, Ames, IA.
[c]FSIS—USDA, Food Safety and Inspection Service, Washington, DC.
[d]CDC—Centers for Disease Control and Prevention, Atlanta, GA.

Example 2

PCR Amplification and Sequencing of the Campylobacter gyrB Gene

Campylobacter strains obtained from the ATCC were grown according to conditions specified by the ATCC. Genomic DNA from these strains and from the E. coli and Salmonella strains listed in Table 1 was extracted using the PrepMan Ultra Reagent (Applied Biosystems, Foster City, Calif.) according to the manufacturer's instructions. DNA from strains obtained from the NADC listed in Table 1, graciously provided by Dr. Irene Wesley (USDA, ARS, NADC), had been purified by cesium chloride density gradient ultracentrifugation and stored at −20° C.

PCR amplification of the gyrB gene for direct sequencing of the PCR products was performed using a GeneAmp 9700 thermal cycler (Applied Biosystems). The universal primer set for PCR amplification of ca. 1,250 bp (1253 or 1256 bp) of the gyrB gene region from all strains was 5'-<u>TAATACGACTCACTATAGGG</u>GTCGACC AVG CNG GNG GNA ART TYG A-3' (SEQ ID NO:1; T7-FWD; T7 promoter sequence attached to 5'-end is underlined) and 5'-<u>GATTTAGGTGACACTATAGCT</u>CGAGCC RTC NAC RTC NGC RTC NGT CAT-3' (SEQ ID NO:2; SP6-REV; SP6 promoter sequence attached to 5'-end is underlined.). One μl of the nucleic acid sample was PCR-amplified in a 100-μl reaction volume containing 1×PCR buffer, 4 mM MgCl2, 0.625 U rTaq DNA polymerase (Takara Bio Inc., Shiga, Japan), 0.2 mM each of the 4 dNTPs, and 0.4 μM of each primer. The cycling conditions were the following: initial denaturation at 95° C. for 5 min, followed by 95° C. for 1 min, annealing at 60° C. for 1 min, and extension at 72° C. for 1 min for 30 cycles. The PCR products were gel-purified after 1.0% (w/v) agarose (Takara Bio Inc., Shiga, Japan) gel electrophoresis using the QIAquick Gel Extraction kit as recommended by the manufacturer (Qiagen, Inc., Valencia, Calif.). Both strands of the purified PCR products were subjected to the cycle sequencing reaction using the ABI PRISM dye terminator cycle sequencing kit (Applied Biosystems). Products were resolved on an ABI Prism 310 automated sequencer (Applied Biosystems). The primers used for DNA sequencing were: 5'-TAA TAG GAC TCA CTA TAG GGG TCG AC-3' (SEQ ID NO:3; T7kai), 5'-GAT TTA GGT GAC ACT ATA GCT CGA G-3' (SEQ ID NO:4; SP6kai). DNA sequences were determined from both strands by extension from the attached-promoter (T7kai and SP6kai primers) sequences and by primer walking.

The gyrB sequences of *C. fetus fetus* (ATCC 15296), *C. fetus* (NADC 5513), *C. fetus Venerealis* (NADC 5519) and *C. hyointestinalis* (ATCC 35217) had a 3-base insertion in position 823-825 in comparison with the same region in the other *Campylobacter* species. The gyrB DNA sequences of *Helicobacter* species from the GeneBank database were compared to the *Campylobacter* sequence data by multiple alignment analysis; considerable differences were observed (data not shown). For example, similarities in the gyrB gene sequence ranged from 38 to 48% between *Campylobacter* species and *Helicobacter pylori*. These data suggest that the from 58.3 to 89.2%, while 6 strains of *C. jejuni* shared identical gyrB gene sequences (data not shown). There was at least 10% interspecies gyrB sequence variation among *Campylobacter* species within the 1020-bp sequenced region studied. The gyrB gene DNA variations were not adequate to discriminate between the subspecies of *C. fetus*; there was no sequence difference between *C. fetus* subsp. *fetus* and *C. fetus* subsp. *venerealis*. There was, however, a 4-base difference without any amino acid sequence changes between *C. fetus* (GenBank accession number: AY330106) and *C. fetus* subsp *fetus* (ATCC 15296).

TABLE 2

Similarity comparison of *Campylobacter* species gyrB gene sequences

| Strain | Similarity (%) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 1 *C. jejuni* NADC[a] 5096 | 100.0 | 89.2 | 65.0 | 60.3 | 63.4 | 64.1 | 69.0 | 66.5 | 66.9 | 79.0 | 77.7 | 82.8 |
| 2 *C. coli* NADC 5095 | | 100.0 | 66.8 | 60.6 | 64.6 | 62.3 | 70.8 | 69.4 | 69.8 | 82.0 | 80.1 | 82.6 |
| 3 *C. concisus* ATCC[a] 33237 | | | 100.0 | 76.5 | 79.8 | 75.7 | 72.8 | 72.9 | 66.8 | 63.2 | 61.2 | 65.1 |
| 4 *C. curvus* ATCC 35224 | | | | 100.0 | 78.0 | 76.4 | 70.2 | 68.8 | 62.5 | 60.7 | 58.7 | 58.3 |
| 5 *C. showae* ATCC 51146 | | | | | 100.0 | 75.6 | 68.9 | 72.2 | 60.5 | 63.8 | 63.2 | 59.9 |
| 6 *C. mucosalis* ATCC 49352 | | | | | | 100.0 | 72.6 | 71.7 | 66.2 | 63.5 | 64.3 | 65.1 |
| 7 *C. fetus fetus* ATCC 15296[b] | | | | | | | 100.0 | 84.0 | 71.9 | 68.1 | 64.7 | 72.4 |
| 8 *C. hyointestinalis* ATCC 35217 | | | | | | | | 100.0 | 67.7 | 64.7 | 62.2 | 68.7 |
| 9 *C. sputorum* biovar *sputorum* ATCC 33562 | | | | | | | | | 100.0 | 66.1 | 63.5 | 71.2 |
| 10 *C. helveticus* ATCC 51210 | | | | | | | | | | 100.0 | 85.6 | 76.7 |
| 11 *C. upsaliensis* ATCC 49816 | | | | | | | | | | | 100.0 | 77.0 |
| 12 *C. lari* ATCC 35221 | | | | | | | | | | | | 100.0 |

[a]NADC, National Animal Disease Center; ATTC, American Type Culture Collection,
[b]There was no sequence difference between *C. fetus* NADC 5513 and *C. fetus* venerealis NADC 5519.

gyrase B gene of *Campylobacter* is superior to the 16S-rDNA gene for species discrimination.

Example 3

Phylogenetic Analysis of DNA Sequences

To evaluate whether differences in gyrB sequences could be employed to reliably discriminate among *Campylobacter* species, it was necessary to quantify the interspecies gyrB DNA sequence variation. The gyrB sequences of 12 species of *Campylobacter* were aligned using the DNASYS Pro program (Version 2.0) (Hitachi, Tokyo, Japan). The data were used as input for phylogenetic analysis using the neighbor-joining method (Saito and Nei. 1987. *Mol. Biol. Evol.* 4: 406-425) and the CLUSTAL W program (Tompson et al. 1994. *Nucleic Acids Res.* 22: 4673-4680) in the DDBJ (DNA Data Bank of Japan) website (www.ddbj.nig.ac.jp/Welcome-e.html). Multiple alignments of 12 *Campylobacter* gyrB sequences were performed, and a matrix representing the sequence variations among the strains analyzed was calculated. Subsequently, a dendrogram was constructed from these data (FIG. 1). Analysis of the dendrogram showed that all 12 *Campylobacter* species were clearly differentiated in the constructed phylogenetic tree. The major topology of the tree based on the partial gyrB gene sequences was similar to one previously reported based on 16S rDNA gene sequence analyses (Gorkiewicz et al., supra).

The similarity analysis of the partial gyrB gene sequences among *Campylobacter* species is shown in Table 2. The similarities of the gyrB DNA sequences among species ranged Example 4

Species-specific Identification by PCR-RFLP

The gyrB sequence data of the different *Campylobacter* spp. were analyzed from a sequence dissimilarity matrix table and by plotting of the Tm value calculated using the nearest-neighbor method. A universal primer mix (Table 3), prepared using primers complementary to the gyrB sequence of each species, was used to amplify a 900 bp gyrB fragment from each *Campylobacter* strain.

One µl of DNA template was amplified in a 100-µl reaction volume containing 1×PCR buffer, 2 mM $MgCl_2$, 0.625 U rTaq (Takara) DNA polymerase, 400 mM of each of the four dNTPs, and the universal primer mixture consisting of 10 nM of each primer in the 12 primer sets (Table 3). The cycling conditions consisted of an initial denaturation at 95° C. for 10 min, followed by 50 cycles of denaturation (95° C. for 15 sec), annealing (65° C. for 1 min), and extension (72° C. for 1 min), with a final 7 min extension at 72° C. The resulting 900-bp PCR products were gel purified after 1% agarose gel electrophoresis as described above. For RFLP analysis, the purified PCR products were digested in a total volume of 20 µl with 5 U or 10 U of DdeI (Toyobo, Osaka, Japan) or XspI (Takara), respectively. The resulting fragments were separated using 6.0% agarose (Agarose X, NipponGene, Tokyo, Japan) prepared in 1× Tris-acetate-EDTA buffer. The gels were stained with the SYBR Green I dye (Invitrogen, Carlsbad, Calif.) as described by the manufacturer, and PCR products were visualized under UV light.

TABLE 3

Primers used in amplification of a 900-bp gyrB gene sequence.

| | Universal mix primer (forward) | Universal mix primer (reverse) |
|---|---|---|
| C. jejuni NADC[a] 5096 | SEQ ID NO: 5 CGTGAAGAATTTTGAGAAGGTAAAGTTATC | SEQ ID NO: 6 TATAGCTTGGAAAGATCTTTCCCTACCTTG |
| C. coli NADC 5095 | SEQ ID NO: 7 CGCCAAGAATTTTCAGAAGGTAAAGTCATC | SEQ ID NO: 8 TATAGCTTGAAAAGATCTTTCTCTACCTTG |
| C. concisus ATCC[a] 33237 | SEQ ID NO: 9 AGACAAGAATTTGCAAAAGGTATCCCTCAA | SEQ ID NO: 10 AATCGCTTGAAAAGATCTTTGTCTTCCTTG |
| C. curvus ATCC 35224 | SEQ ID NO: 11 AGGCAAGAATTTCAAAAAGGTATCCCGGTA | SEQ ID NO: 12 TATCGCCTGAAAAACTCTATCACGTCCTTG |
| C. showae ATCC 51146 | SEQ ID NO: 13 AGACAAGAATTTTCAAAAGGTATCCCTCAA | SEQ ID NO: 14 GATCGCCTGAAATACGCGGTCGCGTCCTTG |
| C. mucosalis ATCC 49352 | SEQ ID NO: 15 AGGCAAGAATTTGCAAAAGGAATTCCAGTA | SEQ ID NO: 16 AATCGCTTGAAATACTCTATCGCGTCCTTG |
| C. fetus fetus ATCC 15296 | SEQ ID NO: 17 CGTCAAGAGTTTTCAAAAGGAATACCCCAA | SEQ ID NQ: 18 AATCGCTTGAAACACACGGTCACGACCCTG |
| C. hyointestinalis ATCC 34217 | SEQ ID NQ: 19 CGCCAAGAATTGGCGGAAGGCATACCTCAA | SEQ ID NO: 20 AATCGCTTGAAACGCTCTATCACGACCTTG |
| C. sputorum sputorum ATCC 33562 | SEQ ID NO: 21 AGACAAGAGTTTTCAAAAGGTGTTCCTACA | SEQ ID NO: 22 TATCGCTTGAAATGCTCTATCACGACCTTG |
| C. helveticus ATCC 51210 | SEQ ID NO: 23 AGACAAGAATTTTCTAAAGGTCTAATTGCA | SEQ ID NO: 24 GATGGCTTGAAAAACTCTATTTCTACCTTG |
| C. upsaliensis ATCC 49816 | SEQ ID NO: 25 CGCCAAGAATTTGGTAAAGGGCAAATAGCT | SEQ ID NO: 26 AATCGCTTGAAAAGCCCTTTCACGCCCCTG |
| C. lari ATCC 35221 | SEQ ID NO: 27 AGACAAGAATTTTCAGAAGGAAAAGTAACA | SEQ ID NO: 28 AATAGCTTGAAAAGTTCTTTCTCTACCTTG |

[a]NADC, National Animal Disease Center; ATTC, American Type Culture Collection.

Figure 3:
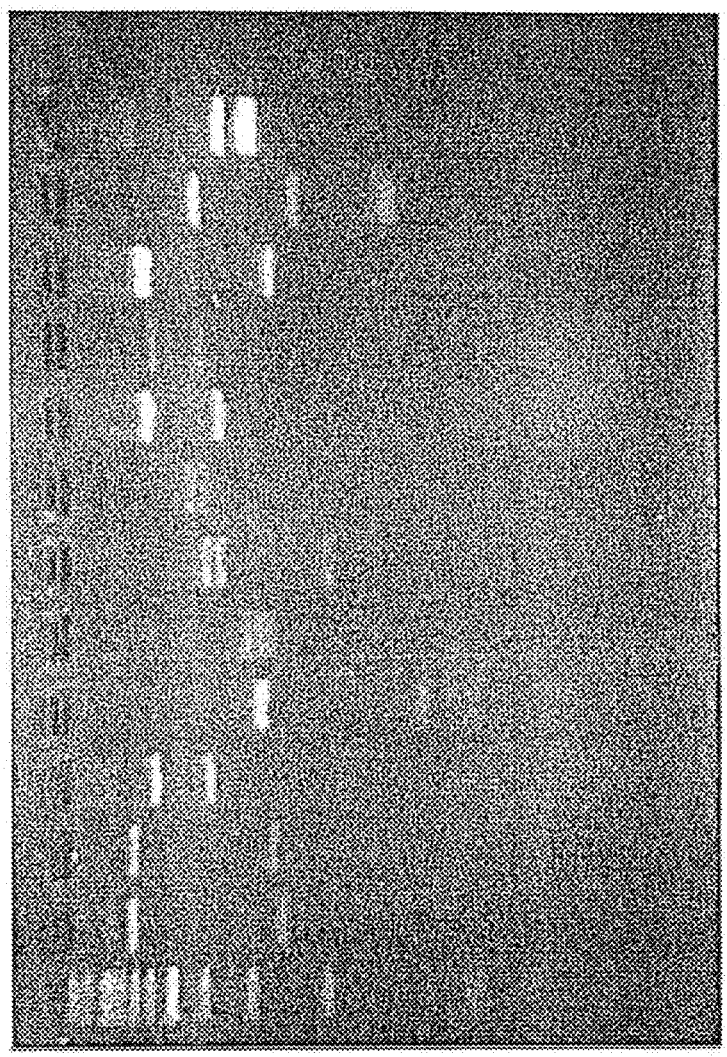
FIG. 3 depicts the PCR-RFLP (DdeI) patterns of *C. jejuni* (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane 9), *C. helveticus* (lane 10), *C. upsaliensis* (lane 11), and *C. lari* (lane 12). Lane M, 100-bp molecular size markers.

PCR amplification using the universal primer mix generated products of the expected size of 900-bp from each Campylobacter strain (FIG. 2). Computational restriction fragment length analyses of the 900-bp amplified region predicted that the DdeI, Hpy188III, and XspI enzymes would generate species-specific digestion patterns. However, Hpy188III was not used in this study because this enzyme can be affected by dam (DNA adenine methylase) and CpG methylation of DNA. In fact, we had difficulty in obtaining reproducible data in RFLP analysis with Hpy188III, since the digestion conditions were difficult to control for this restriction enzyme. It required a low salt concentration in the reaction because of its requirement for bovine serum albumin, which is necessary for enzyme stability. Therefore, only DdeI and XspI were selected for PCR-RFLP analysis in this study. Digestion using either of these two enzymes was expected to generate many fragments less than 200-bp; therefore, 6% agarose gel electrophoresis was used for PCR-RFLP analysis. The PCR RFLP results using DdeI and XspI are shown in FIGS. 3 and 4, respectively. Use of 6% agarose gels demonstrated a resolution comparable to that with polyacrylamide gels for fragments as small as 80-bp. Based on these results, all Campylobacter species studied had species-specific XspI and DdeI digestion patterns, with one exception, namely, that DdeI could not distinguish between C. concisus and C. sputorum. Thus, PCR-RFLP analysis using either DdeI and XspI enzymes, or both, is a valuable tool for accurate discrimination of Campylobacter species. In addition, a computer analysis using the DNASIS program predicted unambiguous identification of the 12 species of Campylobacter by digestion of the gyrB 900-bp region with the restriction enzymes, MboI and HindIII in combination, as a double digestion. This was confirmed experimentally with the 900 bp of PCR product (FIG. 5)

Example 5

PCR with Campylobacter Species-specific Primers and Specificity Testing

Species-specific primer sets for 12 Campylobacter species used in this study were designed based on regions that were dissimilar among the different species. PCR assays with species-specific primers were performed as follows for identification of each Campylobacter species. Template DNA (2.5 µl) diluted 1/10 with sterile distilled water was amplified in a 25-µl reaction volume containing 1× GeneAmp PCR Gold buffer, 0.5 U of AmpliTaq Gold DNA polymerase (Applied Biosystems), 200 µM each of the four dNTPs, and 0.2 µM each of the species-specific primers. The cycling conditions for C. jejuni, C. lari, C. concisus, C. showae, C. curvus, C. fetus, and C. helveticus were the following: initial denaturation at 95° C. for 10 min and 30 cycles of 95° C. for 20 sec, 69° C. for 20 sec, and a final extension for 7 min at 72° C. For C. upsaliensis, C. mucosalis, and for C. hyointestinalis, the annealing time and temperature were 68° C. for 1 min, respectively, and for C. sputorum they were 65° C. for 20 sec, respectively. Cycling conditions were used for amplification of DNA from the different species to obtain an optimal amount of PCR product. The PCR products were analyzed using 2% agarose gel electrophoresis as described above. Primer specificity was evaluated by testing each PCR assay specific for the 12 different *Campylobacter* spp. using genomic DNA from each of the bacteria listed in Table 1. The PCR conditions were the same as those described above, and the PCR products were visualized following agarose gel electrophoresis (2%) and staining with ethidium bromide. All species-specific primers were designed to have similar melting temperatures and to generate PCR products less than 500-bp in length for high PCR efficiency. The species-specific primer sequences and the expected amplicon sizes are shown in Table 4.

Figure 7:
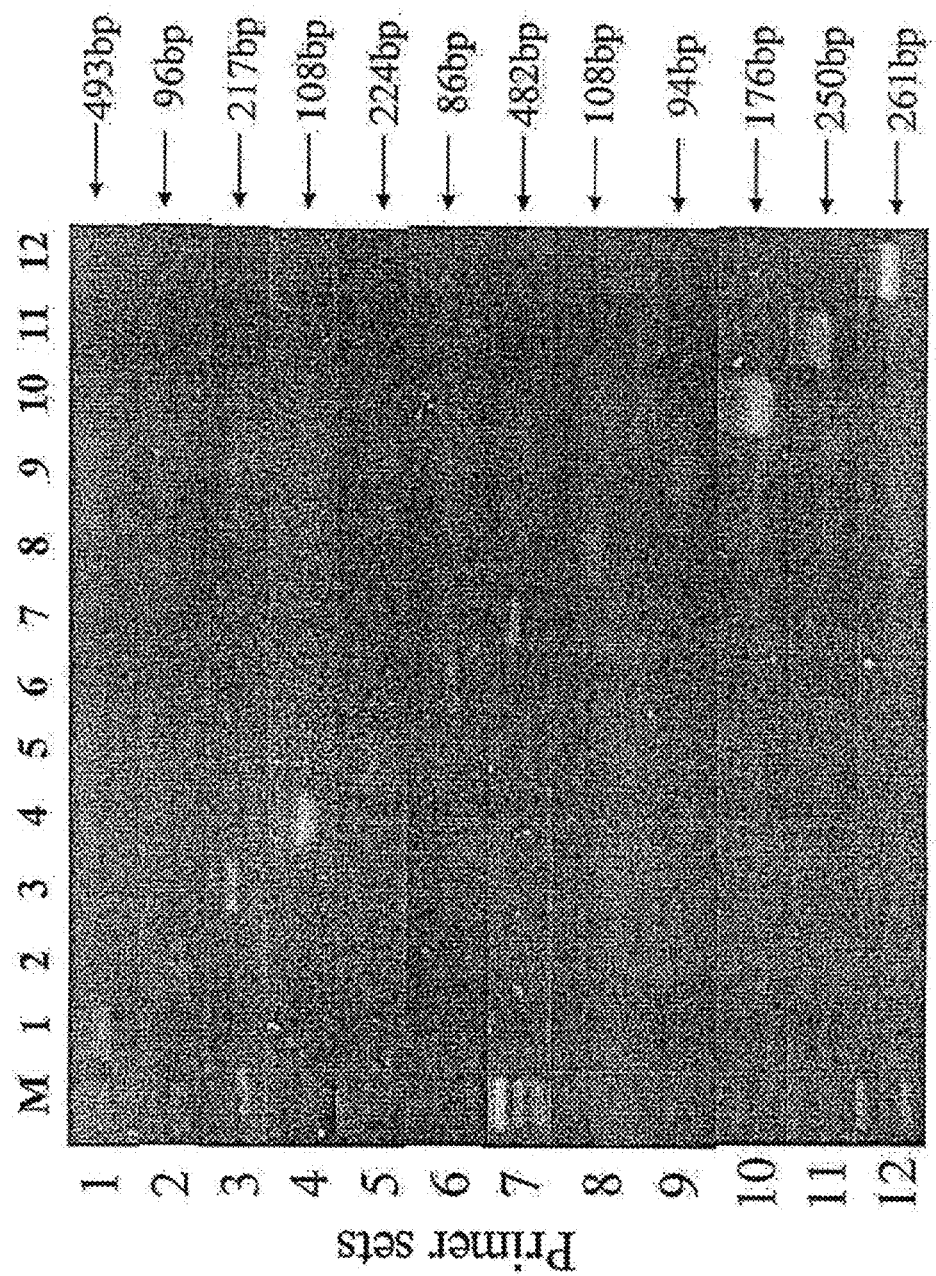
FIG. 7 depicts the species-specific identification of *Campylobacter* species. Each lane represents results of PCR assays using one set of primers and DNA from each of the twelve *Campylobacter* spp. *C. jejuni* primers (lane 1), *C. coli* (lane 2), *C. concisus* (lane 3), *C. curvus* (lane 4), *C. showae* (lane 5), *C. mucosalis* (lane 6), *C. fetus* (lane 7), *C. hyointestinalis* (lane 8), *C. sputorum* (lane 9), *C. helveticus* (lane 10), *C. upsaliensis* (lane 11), and *C. lari* (lane 12). Lane M, 100-bp molecular size markers.

PCR assays using these primers yielded products ranging in size from 86 to 493 bp following amplification of DNA from the different *Campylobacter* spp. These primer sets were specific and amplified the expected PCR product only in each of the respective target *Campylobacter* species (FIG. 6), with no false-positive results using DNA from the non-target *Campylobacter* species (FIG. 7). Furthermore, non-specific bands were not observed with DNA from non-*Campylobacter* strains tested (strains listed in Table 1). Thus, the species-specific primer sets based on gyrB sequences could be very useful for rapid detection and direct identification of *Campylobacter* species by the PCR.

Nucleotide Sequence Accession Numbers

The gyrB gene sequences determined in this study have been deposited in the DDBJ nucleotide sequence database under the following accession numbers: *C. jejuni* gyrB, AB123456; *C. coli* gyrB, AB123456; *C. concisus* gyrB, AB123456; *C. curvus* gyrB, AB123456; *C. showae* gyrB, AB123456; *C. mucosalis* gyrB, AB123456; *C. fetus* gyrB, AB123456; *C. fetus fetus* gyrB, AB123456; *C. fetus venerealis* gyrB, AB123456; *C. hyointestinalis* gyrB, AB123456; *C. sputorum sputorum* gyrB, AB123456; *C. helveticus* gyrB, AB123456; *C. upsaliensis* gyrB, AB123456; and *C. lari* gyrB, AB123456.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

TABLE 4

PCR primers targeting gyrB for *Campylobacter* species-specific identification.

| Strain name | Forward primer | Reverse primer | Amplicon length | Location |
|---|---|---|---|---|
| *C. jejuni* NADC[a] 5096 | SEQ ID NO: 29 AGAATGGGTTTAACTCGTCTGATAAGT | SEQ ID NO: 30 TACCACGCAAAGGCAGTATAGCT | 493 | 84-576 |
| *C. coli* NADC 5095 | SEQ ID NQ: 31 AAATGCTAGTGCTA GGGAAAAAGACCTCT | SEQ ID NO: 32 TGAGGITCAGGCACTTTTACACTTACTAC | 96 | 125-220 |
| *C. concisus* ATCC[a] 33237 | SEQ ID NO: 33 AGCGGGCCTAACAAGAGTTATTACA | SEQ ID NO: 34 TGTAAGCACGTCAAAAACCATCTTT | 217 | 86-302 |
| *C. curvus* ATCC 35224 | SEQ ID NQ: 35 CTGCCAAAGTAAGGACGCAAGTATA | SEQ ID NQ: 36 GGCAAGATCGCCTGAAATACG | 108 | 458-565 |
| *C. showae* ATCC 51146 | SEQ ID NO: 37 AGGGTTTAAGCATAGGAACGCTG | SEQ ID NO: 38 CACCAGATAAAGCTCGCTGATCG | 86 | 415-500 |
| *C. mucosalis* ATCC 49352 | SEQ ID NO: 39 TGCCATTATGAACAAGGCCCTA | SEQ ID NO: 40 TCGCTTGAAACACACGGTCA | 224 | 335-558 |
| *C. fetus fetus* ATCC 15296 | SEQ ID NO: 41 AGAGCTGGGCTTACAAGAGCTATTACA | SEQ ID NO: 42 GGTAAAATCGCTTGAAACGCTCTAT | 482 | 84-565 |
| *C. hyointestinalis* ATCC 35217 | SEQ ID NO: 43 CGGTCAAAAGATGACTTTTGAAGTACTT | SEQ ID NO: 44 GCTTCCCTGCCACGAGCT | 108 | 272-379 |
| *C. sputorm sputorum* ATCC 33562 | SEQ ID NO: 45 AGCTTTACTTGCTGCAAGAGGAAGA | SEQ ID NO: 46 AGGAAGCGTTCCAACAGAAAAGTT | 94 | 350-443 |
| *C. helveticus* ATCC 51210 | SEQ ID NO: 47 CAATAACATACGCACACCAGATGGA | SEQ ID NQ;48 CAGGCACTTTAACGCTCACTATGG | 176 | 38-213 |
| *C. upsaliensis* ATCC 49016 | SEQ ID NO: 49 GCTTACGCGTGTAATTACAAACTATGTC | SEQ ID NO: 50 AATTGCCTTAGCCTCGATAGGG | 250 | 92-341 |
| *C. lari* ATCC 35221 | SEQ ID NO: 51 CTATGTTCGTCCTATAGTTTCTAAGGTTC | SEQ ID NO: 52 CCAGCACTATCCACCCTCAACTAAATAA | 261 | 257-517 |

[a]NADC, National Animal Disease Center; ATTC, American Type Culture Collection.

We claim:

1. A method of speciating *Campylobacter* by polymerase chain reaction (PCR) restriction fragment length polymorphism (RFLP), said method comprising:

a) providing a standard sample mixture of DNA of each *Campylobacter* species (spp.): *C. jejuni, C. coli, C. concisus, C. curvus, C. showae, C. mucosalis, C. fetus fetus, C. hyointestinalis, C. sputorum sputorum, C. helveticus, C. upsaliensis* and *C. lari* or providing a test sample mixture suspected of containing DNA of any or all of said *Campylobacter* spp.;

b) amplifying a target sequence of DNA of all of the *Campylobacter* spp. in said standard or test sample mixture, wherein said target sequence is the gyrB sequence of each *Campylobacter* spp. present in said standard or test sample mixture, by adding a mixture of the following primer sets to the standard or test sample mixture wherein the primer set mixture comprises oligonucleotide primers complementary to the gyrB sequence of all of the following *Campylobacter* species; comprising, *C. jejuni* wherein said primer set consists of CGTCAA-GAATTTTCAGAAGGTAAAGTTATC (SEQ ID NO:5) and TATAGCTTGGAAAGATCTTTCCCTAC-CTTG (SEQ ID NO: 6), *C. coli* wherein said primer set consists of CGCCAAGAATTTTCAGAAGG-TAAAGTCATC (SEQ ID NO:7) and TATAGCT-TGAAAAGATCTTTCTCTACCTTG (SEQ ID NO:8), *C. concisus* wherein said primer set consists of AGA-CAAGAATTTGCAAAAGGTATC CCTCAA (SEQ ID NO:9) and AATCGCTTGAAAAGATCTTTCTCTTC-CTTG (SEQ ID NO: 10), *C. curvus wherein said primer set consists of AGGCAAGAATTTCAA AAAGGTATC-CCGGTA (SEQ ID NO:*11) and TATCGCCT-GAAAAACTCTATCAC GTCCTTG (SEQ ID NO: 12), *C. showae* wherein said primer set consists of AGA-CAAGAATTTTCAAAAGGTATCCCTCAA (SEQ ID NO: 13) and GATCGCCT GAAATACGCG-GTCGCGTCCTTG (SEQ ID NO: 14), *C. mucosalis* wherein said primer set consists of AGGCAA-GAATTTGCAAAAGGAATTCCAGTA (SEQ ID NO: 15) and AATCGCTTGAAATACTCTATCGCGTC-CTTG (SEQ ID NO: 16), *C. fetus fetus* wherein said primer set consists of CGTCAAGAGTTTTCAAAAG-GAA TACCC CAA (SEQ ID NO: 17) and AATCGCT-TGAAACACACGGTCACGACC CTG (SEQ ID NO: 18), *C. hyointestinalis* wherein said primer set consists of CGCCAAGAATTCGCCGAAGGCATACCTCAA (SEQ ID NO: 19) and AATCGC TTGAAACGCTCTAT-CACGACCTTG (SEQ ID NO: 20), *C. sputorum sputorum* wherein said primer set consists of AGACAA-GAGTTTTCAAAAGGTGTTCCT ACA (SEQ ID NO: 21) and TATCGCTTGAAA TGCTCTATCACGAC-CTTG (SEQ ID NO: 22), *C. helveticus* wherein said primer set consists of AGACAAGAATTTT CTAAAG-GTCTAATTGCA (SEQ ID NO: 23) and GATGGCT-TGAAAAACTCTATT TCTACCTTG (SEQ ID NO: 24), *C. upsaliensis* wherein said primer set consists of CGCCAAGAATTTGCTAAAGGGCAAATAGCT (SEQ ID NO: 25) and AATCGCTT GAAAAGC-CCTTTCACGCCCCTG (SEQ ID NO:26), and *C. lari* wherein said primer set consists of AGACAA-GAATTTTCAGAAGGAAAAGTAACA (SEQ ID NO: 27) and AATAGCTTGAAAAGTTCTTTCTCTAC-CTTG (SEQ ID NO: 28);

c) obtaining amplification products of the target sequence of DNA of all *Campylobacter* spp. in said standard or test sample mixture as an indication of the presence of *Campylobacter* species, wherein all of said *Campylobacter* spp. present in the standard or test sample mixture can be identified;

d) digesting the DNA amplification products obtained by PCR with the restriction enzymes Ddel or Xspl;

e) analyzing the restriction fragment length polymorphisms resulting from said digesting step by gel electrophoresis; and f) identifying all species and strains of *Campylobacter* spp. in said standard or test sample mixture by their RFLP patterns, identification resulting from a comparison of said RFLP patterns to the standard RFLP patterns generated when a standard mixture known to contain gyrB DNA of all said species and strains of *Campylobacter* spp. is analyzed using said mixture consisting of all said oligonucleotide primers complementary to the gyrB sequence of all said *Campylobacter* spp.

2. A method of speciating *Campylobacter* by polymerase chain reaction, said method comprising:

a) providing a standard sample mixture of DNA of each *Campylobacter* species (spp.): *C. jejuni, C. coli, C. concisus, C. curvus, C. showae, C. mucosalis, C. fetus fetus, C. hyointestinalis, C. sputorum sputorum, C. helveticus, C. upsaliensis* and *C. lari* or providing a test sample mixture suspected of containing DNA of any or all of said *Campylobacter* spp.;

b) amplifying a target sequence of DNA of all of the *Campylobacter* spp. in said sample mixture, wherein said target sequence is the gyrB sequence of each *Campylobacter* spp. present in said standard or test sample mixture, by adding a mixture of the following species-specific primer sets complementary to the gyrB sequence of all of the following *Campylobacter* species; comprising, *C. jejuni* wherein said primer set consists of AGAATGGGTTTAACTCGTGTGATAAGT (SEQ ID NO:29) and TACCACGCA AAGGCAGTATAGCT (SEQ ID NO: 30), *C. coli* wherein said primer set consists of AAATGCTAGTGCTAGG-GAAAAAGACTCT (SEQ ID NO:31) and TGAGGT TCAGGCACTTTTACACTTACTAC (SEQ ID NO:32), *C. concisus* wherein said primer set consists of AGCGGGCCTAACAAGAGTT ATTACA (SEQ ID NO:33) and TGTAAGCACGTCAAAAACCATCTTT (SEQ ID NO: 34), *C. curvus* wherein said primer set consists of CTGCCAAAGTAAGGAC GCAAGTATA (SEQ ID NO:35) and GGCAAGATCGCCT-GAAATACG (SEQ ID NO: 36); *C. showae* wherein said primer set consists of AGGGTTTAAGCATA GGAACGCTG (SEQ ID NO: 37) and CACCA-GATAAAGCTCGCTGATCG (SEQ ID NO: 38), *C. mucosalis* wherein said primer set consists of TGCGAT-TATGAA CAAGGCCCTA (SEQ ID NO: 39) and TCGCTTGAAACACACGGTCA (SEQ ID NO: 40), *C. fetus fetus* wherein said primer set consists of AGAGCTGGGCTTAC AAGAGCTATTACA (SEQ ID NO: 41) and GGTAAAATCGCTTGAAACGCTCTAT (SEQ ID NO: 42), *C. hyointestinalis* wherein said primer set consists of CGGTCA AAAGAT-GACTTTTGAAGTACTT (SEQ ID NO: 43) and GCT-TCCCTGCCACGA GCT (SEQ ID NO: 44), *C. sputorum sputorum* wherein said primer set consists of AGCTTTACTTGCTGCAAGAGGAAGA (SEQ ID NO: 45) and AGGAAGCGTTCC AACAGAAAA GTT (SEQ ID NO: 46), *C. helveticus* wherein said primer set consists of CAATA ACATACGCACACCAGATGGA (SEQ ID NO: 47) and CAGGCACTTTAACGCTCAC-TATGG (SEQ ID NO: 48), *C. upsaliensis* wherein said primer set consists of GCTTACGCGTGTAATTA-CAAACTATGTC (SEQ ID NO: 49) and AATTGCCT-TAGCCTCGATAGGG (SEQ ID NO: 50) and *C. lari* wherein said primer set consists of CTATGTTCGTC-CTATAGTTTCTAAGGCTTC (SEQ ID NO: 51) and CCAGCACTATCACCCTCAACTAAATAA (SEQ ID NO: 52); and c) rapidly detecting the presence of amplification products of the target sequence of DNA of all *Campylobacter* spp. in said standard or test sample mixture and directly identifying the presence of all species and strains of *Campylobacter* spp. in said sample, wherein said amplification product of 493 bp identifies *C. jejuni*, said amplification product of 96 bp identifies *C. coli*, said amplification product of 217 bp identifies *C. concisus*, said amplification product of 108 bp identifies *C. curvus*, said amplification product of 86 bp identifies *C. showae*, said amplification product of 224 bp identifies *C. mucosalis*, said amplification product of 482 bp identifies *C. fetus fetus*, said amplification product of 108 bp identifies *C. hyointestinalis*, said amplification product of 94 bp identifies *C. sputorum sputorum*, said amplification product of 176 bp identifies *C. helveticus*, said amplification product of 250 bp identifies *C. upsaliensis*, said amplification product of 261 bp identifies *C. lari*.

3. A method of speciating *Campylobacter* by polymerase chain reaction (PCR) restriction fragment length polymorphism (RFLP), said method comprising:
 a) providing a standard sample mixture of DNA of each *Campylobacter* species (spp.): *C. jejuni, C. coli, C. concisus, C. curvus, C. showae, C. mucosalis, C. fetus fetus, C. hyointestinalis, C. sputorum sputorum, C. helveticus, C. upsaliensis* and *C. lari* or providing a test sample mixture suspected of containing DNA of any or all of said *Campylobacter* spp.;
 b) amplifying a target sequence of DNA of all of the *Campylobacter* spp. in said standard or test sample mixture, wherein said target sequence is the gyrB sequence of each *Campylobacter* spp. present in said standard or test sample mixture, by adding a mixture of the following primer sets to the standard or test sample mixture wherein the primer set mixture comprises oligonucleotide primers complementary to the gyrB sequence of all of the following *Campylobacter* species; comprising, *C. jejuni* wherein said primer set consists of CGTCAAGAATTTTCAGAAGGTAAAGTT ATC (SEQ ID NO:5) and TATAGCTTGGAAAGATCTTTCCCTAC-CTTG (SEQ ID NO: 6), *C. coli* wherein said primer set consists of CGCCAAGAATTTTCAGAAGG-TAAAGTCATC (SEQ ID NO:7) and TATAGCT-TGAAAAGATCTTTCTCTACCTTG (SEQ ID NO:8), *C. concisus* wherein said primer set consists of AGA-CAAG AATTTGCAAAAGGT ATCCCTCAA (SEQ ID NO:9) and AATCGCTTGAAAAGATCTTTCTCTTC-CTTG (SEQ ID NO: 10), *C. curvus* wherein said primer set consists of AGGCAAGAATT TCAAAAAGG-TATCCCGGTA (SEQ ID NO:11) and TATCGCCT-GAAAAACTCT ATCACGTCCTTG (SEQ ID NO: 12), *C. showae* wherein said primer set consists of AGA-CAAGAATTTTCAAAAGGTATCCCTCAA (SEQ ID NO: 13) and GATCGC CTGAAATACGCG-GTCGCGTCCTTG (SEQ ID NO: 14), *C. mucosalis* wherein said primer set consists of AGGCAA-GAATTTGCAAAAGGAATTCCAGTA (SEQ ID NO: 15) and AATCGCTTGAAATACTCTATCGCGTC-CTTG (SEQ ID NO: 16), *C. fetus fetus* wherein said primer set consists of CGTCAAGAGTTTTCAAAAG GAATACCCCAA (SEQ ID NO: 17) and AATCGCT-TGAAACACACGGTCACG ACC CTG (SEQ ID NO: 18), *C. hyointestinalis* wherein said primer set consists of CGCCAAGAATTCGCCGAAGGCATACCTCAA (SEQ ID NO: 19) and AATCGCT TGAAACGCTCTAT-CACGACCTTG (SEQ ID NO: 20), *C. sputorum sputorum* wherein said primer set consists of AGACAA-GAGTTTTCAAAAGGTGTTCCT ACA (SEQ ID NO: 21) and TATCGCTTGAAATGCTCTATCACGAC-CTTG (SEQ ID NO: 22), *C. helveticus* wherein said primer set consists of AGACAAGAATTT TCTAAAG-GTCTAATTGCA (SEQ ID NO: 23) and GATGGCT-TGAAAAACTCTAT TTCTACCTTG (SEQ ID NO: 24), *C. upsaliensis* wherein said primer set consists of CGCCAAGAATTTGCTAAAGGGCAAATAGCT (SEQ ID NO: 25) and AATCGC TTGAAAAGC-CCTTTCACGCCCTG (SEQ ID NO:26), and *C. lari* wherein said primer set consists of AGACAA-GAATTTTCAGAAGGAAAAGTAACA (SEQ ID NO: 27) and AATAGCTTGAAAAGTTCTTTCTCTAC-CTTG (SEQ ID NO: 28);
 c) obtaining amplification products of the target sequence of DNA of all *Campylobacter* spp. in said standard or test sample mixture as an indication of the presence of *Campylobacter* species, wherein all of said *Campylobacter* spp. present in the standard or test sample mixture can be identified;
 d) digesting the DNA amplification products obtained by PCR with the restriction enzymes MboI and HindIII in combination, as a double digestion;
 e) analyzing the restriction fragment length polymorphisms resulting from said digesting step by gel electrophoresis; and
 f) identifying all species and strains of *Campylobacter* spp. in said standard or test sample mixture by their RFLP patterns, identification resulting from a comparison of said RFLP patterns to the standard RFLP patterns generated when a standard mixture known to contain gyrB DNA of all said species and strains of *Campylobacter* spp. is analyzed using said mixture consisting of all said oligonucleotide primers complementary to the gyrB sequence of all said *Campylobacter* spp.

4. A composition for detecting and identifying any or all of twelve *Campylobacter* species (spp.) in a test sample by polymerase chain reaction (PCR) restriction fragment length polymorphism (RFLP), said composition comprising: a mixture of primer sets according to claims 1 and 3 wherein the mixture comprises oligonucleotide primers complementary to the gyrB sequence of all of the following *Campylobacter* species spp. and capable of identifying all species and strains of *Campylobacter* spp. following PCR-RFLP, said mixture comprising the primer set CGTCAAGAATTTTCA GAAG-GTAAAGTTATC (SEQ ID NO:5) and TATAGCTTGGAAAA-GATCTTTCCCTAC CTTG (SEQ ID NO: 6) for *C. jejuni*, the primer set CGCCAAGAATTTTCAGAAGGTAAA GTCATC (SEQ ID NO:7) and TATAGCTTGAAAA-GATCTTTCTCTACCTTG (SEQ ID NO:8) for *C. coli*, the primer set AGACAAGAATTTGCAAAAGGTATCCCT-CAA (SEQ ID NO:9) and AATCGCTTGAAAA-GATCTTTCTCTTCCTTG (SEQ ID NO: 10) for *C. concisus*, the primer set AGGCAAGAATTTCAAAAAGGTATCCCGGTA (SEQ ID NO:11) and TATCGCCTGAAA AACTCTATCACGTC-CTTG (SEQ ID NO: 12) for *C. curvus*, the primer set AGA-CAAGAATTTTCAAAAGGTATCCCTCAA (SEQ ID NO: 13) and GATCGCCTGAAATACGCGGTCGCGTCCTTG (SEQ ID NO: 14) for *C. showae*, the primer set AGGCAA-GAATTTGCAAAAGGAATTCCAGTA (SEQ ID NO: 15) and AATCGCTTGAAATACTCTATCGCGTCCTTG (SEQ ID NO: 16) for *C. mucosalis*, the primer set CGTCAA-GAGTTTTCAAAAGGAATACCCCAA (SEQ ID NO: 17) and AATCGCTTGAAACACACGGTCACGACCCTG (SEQ ID NO: 18) for *C. fetus fetus*, the primer set CGCCAA-GAATTCGCCGAAGGCATACCTCAA (SEQ ID NO: 19) and AATCGCTTGAAACGCTCTATCACGACCTTG (SEQ ID NO: 20) for *C. hyointestinalis*, the primer set AGACAA-GAGTTTTCAAAAGGTGTTCCTACA (SEQ ID NO: 21) and TATCGCTTGAAATGCTCTATCACGACCTTG (SEQ ID NO: 22) for *C. sputorum sputorum*, the primer set AGA-CAAGAATTTTCTAAAGGTCTAATTGCA (SEQ ID NO: 23) and GATGGCTTGAAAAACTCTATTTCTACCTTG (SEQ ID NO: 24) for *C. helveticus*, the primer set CGCCAA-GAATTTGCTAAAGGGCAAATAGCT (SEQ ID NO: 25) and AATCGCTTGAAAAGCCCTTTCACGCCCTG (SEQ ID NO:26) for *C. upsaliensis*, and the primer set AGACAA-GAATTTTCAGAAGGAAAAGTAACA (SEQ ID NO: 27) and AATAGCTTGAAAAGTTCTTTCTCTACCTTG (SEQ ID NO: 28) for detecting *C. lari*; and the restriction enzymes DdeI or XspI, or the combination of MboI and HindIII.

5. A composition for detecting and identifying any or all of twelve *Campylobacter* species (spp.) in a test sample by polymerase chain reaction (PCR), said composition comprising: a mixture of primer sets according to claim 2 wherein said mixture comprises oligonucleotide primers complementary to the gyrB sequence of all of the following *Campylobacter* species spp. and capable of identifying all species and strains of *Campylobacter* spp. following PCR, said mixture comprising the primer set AGAATGGGTTTAACTCGTGT-GATAAGT (SEQ ID NO:29) and TACCACGCAAAGGC AGTATAGCT (SEQ ID NO: 30) for *C. jejuni*, the primer set AAATGCTAGTGCTAGGGA A AAAGACTCT (SEQ ID NO:31) and TGAGGTTCAGGCACTTTTACACTTACTAC (SEQ ID NO:32) for *C. coli*, the primer set AGCGGGC-CTAACAAGAGTTATTACA (SEQ ID NO:33) and TGTAAGCACGTCAAAAACCATCTTT (SEQ ID NO: 34) for *C. concisus*, the primer set CTGCCAAAGTAAGGACG-CAAGTATA (SEQ ID NO:35) and GGCAAGATCGCCT-GAAATACG (SEQ ID NO: 36) for *C. curvus*, the primer set AGGGTTTAAGCATAGGAACGCTG (SEQ ID NO: 37) and CACCAG ATAAAGCTCGC TGATCG (SEQ ID NO: 38) for *C. showae*, the primer set TGCGATTATGAACAAGGCC CTA (SEQ ID NO: 39) and TCGCTTGAAACACACG-GTCA (SEQ ID NO: 40) for *C. mucosalis*, the primer set AGAGCTGGGCTTACAAGAGCTATTACA (SEQ ID NO: 41) and GGTAAAATCGCTTGAAACGCTCTAT (SEQ ID NO: 42) for *C. fetus fetus*, the primer set CGGTCAAAAGAT-GACTTTTGAAGTACTT (SEQ ID NO: 43) and GCTTCCC TGCCACGAGCT (SEQ ID NO: 44) for *C. hyointestinalis*, the primer set AGCTTTACTTG CTGCAAGAGGAAGA (SEQ ID NO: 45) and AGGAAGCGTTCCAACA-GAAAAGTT (SEQ ID NO: 46) for *C. sputorum sputorum*, the primer set CAATAACATACGCACACCA GATGGA (SEQ ID NO: 47) and CAGGCACTTTAACGCTCAC-TATGG (SEQ ID NO: 48) for *C. helveticus*, the primer set GCTTACGCGTGTAATTACAAACTATGTC (SEQ ID NO: 49) and AATTGCCTTAGCCTCGATAGGG (SEQ ID NO:50) for *C. upsaliensis*, and the primer set CTATGT-TCGTCCTATAGTTTCTAAGGCTTC (SEQ ID NO: 51) and CCAGCACTATCACCCTCAACTAAATAA (SEQ ID NO: 52) for *C. lari*; and a polymerase.

6. The method of claim 2, wherein amplification takes place under real-time PCR conditions and the amplification products are detected and quantitated by real-time analysis.

7. The method of claim 1, wherein amplification takes place under real-time PCR conditions and the amplification products are detected and quantitated by real-time analysis.

8. The method of claim 3, wherein amplification takes place under real-time PCR conditions and the amplification products are detected and quantitated by real-time analysis.

* * * * *

SEQUENCE LISTING

<160> NUMBER OF SEQ ID NOS: 52

<210> SEQ ID NO 1
<211> LENGTH: 46
<212> TYPE: DNA
<213> ORGANISM: Campylobacter sp.
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 1
taatacgact cactataggg gtcgaccayg cnggnggnaa rttyga         46

<210> SEQ ID NO 2
<211> LENGTH: 48
<212> TYPE: DNA
<213> ORGANISM: Campylobacter sp.
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 2
gatttaggtg acactatagc tcgagccrtc nacrtcngcr tcngtcat         48

<210> SEQ ID NO 3
<211> LENGTH: 26
<212> TYPE: DNA
<213> ORGANISM: Campylobacter sp.

<400> SEQUENCE: 3
taatacgact cactataggg gtcgac         26

<210> SEQ ID NO 4
<211> LENGTH: 25
<212> TYPE: DNA
<213> ORGANISM: Campylobacter sp.

<400> SEQUENCE: 4
gatttaggtg acactatagc tcgag         25

<210> SEQ ID NO 5
<211> LENGTH: 30
<212> TYPE: DNA
<213> ORGANISM: Campylobacter jejuni

<400> SEQUENCE: 5
cgtcaagaat tttcagaagg taaagttatc         30

<210> SEQ ID NO 6

```
<211> LENGTH: 30
<212> TYPE: DNA
<213> ORGANISM: Campylobacter jejuni

<400> SEQUENCE: 6
tatagcttgg aaagatcttt ccctaccttg                                        30

<210> SEQ ID NO 7
<211> LENGTH: 30
<212> TYPE: DNA
<213> ORGANISM: Campylobacter coli

<400> SEQUENCE: 7
cgccaagaat tttcagaagg taaagtcatc                                        30

<210> SEQ ID NO 8
<211> LENGTH: 30
<212> TYPE: DNA
<213> ORGANISM: Campylobacter coli

<400> SEQUENCE: 8
tatagcttga aaagatcttt ctctaccttg                                        30

<210> SEQ ID NO 9
<211> LENGTH: 30
<212> TYPE: DNA
<213> ORGANISM: Campylobacter concisus

<400> SEQUENCE: 9
agacaagaat ttgcaaaagg tatccctcaa                                        30

<210> SEQ ID NO 10
<211> LENGTH: 30
<212> TYPE: DNA
<213> ORGANISM: Campylobacter concisus

<400> SEQUENCE: 10
aatcgcttga aaagatcttt ctcttccttg                                        30

<210> SEQ ID NO 11
<211> LENGTH: 30
<212> TYPE: DNA
<213> ORGANISM: Campylobacter curvus

<400> SEQUENCE: 11
aggcaagaat ttcaaaaagg tatcccggta                                        30

<210> SEQ ID NO 12
<211> LENGTH: 30
<212> TYPE: DNA
<213> ORGANISM: Campylobacter curvus

<400> SEQUENCE: 12
tatcgcctga aaaactctat cacgtccttg                                        30

<210> SEQ ID NO 13
<211> LENGTH: 30
<212> TYPE: DNA
<213> ORGANISM: Campylobacter showae

<400> SEQUENCE: 13
agacaagaat tttcaaaagg tatccctcaa                                        30

<210> SEQ ID NO 14
```

-continued

```
<211> LENGTH: 30
<212> TYPE: DNA
<213> ORGANISM: Campylobacter showae

<400> SEQUENCE: 14
gatcgcctga aatacgcggt cgcgtccttg                                          30

<210> SEQ ID NO 15
<211> LENGTH: 30
<212> TYPE: DNA
<213> ORGANISM: Campylobacter mucosalis

<400> SEQUENCE: 15
aggcaagaat ttgcaaaagg aattccagta                                          30

<210> SEQ ID NO 16
<211> LENGTH: 30
<212> TYPE: DNA
<213> ORGANISM: Campylobacter mucosalis

<400> SEQUENCE: 16
aatcgcttga aatactctat cgcgtccttg                                          30

<210> SEQ ID NO 17
<211> LENGTH: 30
<212> TYPE: DNA
<213> ORGANISM: Campylobacter fetus

<400> SEQUENCE: 17
cgtcaagagt tttcaaaagg aataccccaa                                          30

<210> SEQ ID NO 18
<211> LENGTH: 30
<212> TYPE: DNA
<213> ORGANISM: Campylobacter fetus

<400> SEQUENCE: 18
aatcgcttga aacacacggt cacgaccctg                                          30

<210> SEQ ID NO 19
<211> LENGTH: 30
<212> TYPE: DNA
<213> ORGANISM: Campylobacter hyointestinalis

<400> SEQUENCE: 19
cgccaagaat tcgccgaagg catacctcaa                                          30

<210> SEQ ID NO 20
<211> LENGTH: 30
<212> TYPE: DNA
<213> ORGANISM: Campylobacter hyointestinalis

<400> SEQUENCE: 20
aatcgcttga aacgctctat cacgaccttg                                          30

<210> SEQ ID NO 21
<211> LENGTH: 30
<212> TYPE: DNA
<213> ORGANISM: Campylobacter sputorum

<400> SEQUENCE: 21
agacaagagt tttcaaaagg tgttcctaca                                          30

<210> SEQ ID NO 22
```

-continued

```
<211> LENGTH: 30
<212> TYPE: DNA
<213> ORGANISM: Campylobacter sputorum

<400> SEQUENCE: 22
tatcgcttga aatgctctat cacgaccttg                                          30

<210> SEQ ID NO 23
<211> LENGTH: 30
<212> TYPE: DNA
<213> ORGANISM: Campylobacter helveticus

<400> SEQUENCE: 23
agacaagaat tttctaaagg tctaattgca                                          30

<210> SEQ ID NO 24
<211> LENGTH: 30
<212> TYPE: DNA
<213> ORGANISM: Campylobacter helveticus

<400> SEQUENCE: 24
gatggcttga aaaactctat ttctaccttg                                          30

<210> SEQ ID NO 25
<211> LENGTH: 30
<212> TYPE: DNA
<213> ORGANISM: Campylobacter upsaliensis

<400> SEQUENCE: 25
cgccaagaat ttgctaaagg gcaaatagct                                          30

<210> SEQ ID NO 26
<211> LENGTH: 30
<212> TYPE: DNA
<213> ORGANISM: Campylobacter upsaliensis

<400> SEQUENCE: 26
aatcgcttga aaagcccttt cacgcccctg                                          30

<210> SEQ ID NO 27
<211> LENGTH: 30
<212> TYPE: DNA
<213> ORGANISM: Campylobacter lari

<400> SEQUENCE: 27
agacaagaat tttcagaagg aaaagtaaca                                          30

<210> SEQ ID NO 28
<211> LENGTH: 30
<212> TYPE: DNA
<213> ORGANISM: Campylobacter lari

<400> SEQUENCE: 28
aatagcttga aaagttcttt ctctaccttg                                          30

<210> SEQ ID NO 29
<211> LENGTH: 27
<212> TYPE: DNA
<213> ORGANISM: Campylobacter jejuni

<400> SEQUENCE: 29
agaatgggtt taactcgtgt gataagt                                             27

<210> SEQ ID NO 30
```

```
<211> LENGTH: 23
<212> TYPE: DNA
<213> ORGANISM: Campylobacter jejuni

<400> SEQUENCE: 30
taccacgcaa aggcagtata gct                                              23

<210> SEQ ID NO 31
<211> LENGTH: 28
<212> TYPE: DNA
<213> ORGANISM: Campylobacter coli

<400> SEQUENCE: 31
aaatgctagt gctagggaaa aagactct                                         28

<210> SEQ ID NO 32
<211> LENGTH: 29
<212> TYPE: DNA
<213> ORGANISM: Campylobacter coli

<400> SEQUENCE: 32
tgaggttcag gcacttttac acttactac                                        29

<210> SEQ ID NO 33
<211> LENGTH: 25
<212> TYPE: DNA
<213> ORGANISM: Campylobacter concisus

<400> SEQUENCE: 33
agcgggccta acaagagtta ttaca                                            25

<210> SEQ ID NO 34
<211> LENGTH: 25
<212> TYPE: DNA
<213> ORGANISM: Campylobacter concisus

<400> SEQUENCE: 34
tgtaagcacg tcaaaaacca tcttt                                            25

<210> SEQ ID NO 35
<211> LENGTH: 25
<212> TYPE: DNA
<213> ORGANISM: Campylobacter curvus

<400> SEQUENCE: 35
ctgccaaagt aaggacgcaa gtata                                            25

<210> SEQ ID NO 36
<211> LENGTH: 21
<212> TYPE: DNA
<213> ORGANISM: Campylobacter curvus

<400> SEQUENCE: 36
ggcaagatcg cctgaaatac g                                                21

<210> SEQ ID NO 37
<211> LENGTH: 23
<212> TYPE: DNA
<213> ORGANISM: Campylobacter showae

<400> SEQUENCE: 37
agggtttaag cataggaacg ctg                                              23

<210> SEQ ID NO 38
```

```
<211> LENGTH: 23
<212> TYPE: DNA
<213> ORGANISM: Campylobacter showae

<400> SEQUENCE: 38
caccagataa agctcgctga tcg                                            23

<210> SEQ ID NO 39
<211> LENGTH: 22
<212> TYPE: DNA
<213> ORGANISM: Campylobacter mucosalis

<400> SEQUENCE: 39
tgcgattatg aacaaggccc ta                                             22

<210> SEQ ID NO 40
<211> LENGTH: 20
<212> TYPE: DNA
<213> ORGANISM: Campylobacter mucosalis

<400> SEQUENCE: 40
tcgcttgaaa cacacggtca                                                20

<210> SEQ ID NO 41
<211> LENGTH: 27
<212> TYPE: DNA
<213> ORGANISM: Campylobacter fetus

<400> SEQUENCE: 41
agagctgggc ttacaagagc tattaca                                        27

<210> SEQ ID NO 42
<211> LENGTH: 25
<212> TYPE: DNA
<213> ORGANISM: Campylobacter fetus

<400> SEQUENCE: 42
ggtaaaatcg cttgaaacgc tctat                                          25

<210> SEQ ID NO 43
<211> LENGTH: 28
<212> TYPE: DNA
<213> ORGANISM: Campylobacter hyointestinalis

<400> SEQUENCE: 43
cggtcaaaag atgacttttg aagtactt                                       28

<210> SEQ ID NO 44
<211> LENGTH: 18
<212> TYPE: DNA
<213> ORGANISM: Campylobacter hyointestinalis

<400> SEQUENCE: 44
gcttccctgc cacgagct                                                  18

<210> SEQ ID NO 45
<211> LENGTH: 25
<212> TYPE: DNA
<213> ORGANISM: Campylobacter sputorum

<400> SEQUENCE: 45
agctttactt gctgcaagag gaaga                                          25

<210> SEQ ID NO 46
```

```
<211> LENGTH: 24
<212> TYPE: DNA
<213> ORGANISM: Campylobacter sputorum

<400> SEQUENCE: 46
aggaagcgtt ccaacagaaa agtt                                          24

<210> SEQ ID NO 47
<211> LENGTH: 25
<212> TYPE: DNA
<213> ORGANISM: Campylobacter helveticus

<400> SEQUENCE: 47
caataacata cgcacaccag atgga                                         25

<210> SEQ ID NO 48
<211> LENGTH: 24
<212> TYPE: DNA
<213> ORGANISM: Campylobacter helveticus

<400> SEQUENCE: 48
caggcacttt aacgctcact atgg                                          24

<210> SEQ ID NO 49
<211> LENGTH: 28
<212> TYPE: DNA
<213> ORGANISM: Campylobacter upsaliensis

<400> SEQUENCE: 49
gcttacgcgt gtaattacaa actatgtc                                      28

<210> SEQ ID NO 50
<211> LENGTH: 22
<212> TYPE: DNA
<213> ORGANISM: Campylobacter upsaliensis

<400> SEQUENCE: 50
aattgcctta gcctcgatag gg                                            22

<210> SEQ ID NO 51
<211> LENGTH: 30
<212> TYPE: DNA
<213> ORGANISM: Campylobacter lari

<400> SEQUENCE: 51
ctatgttcgt cctatagttt ctaaggcttc                                    30

<210> SEQ ID NO 52
<211> LENGTH: 27
<212> TYPE: DNA
<213> ORGANISM: Campylobacter lari

<400> SEQUENCE: 52
ccagcactat caccctcaac taaataa                                       27
```